United States Patent
Nevo et al.

(10) Patent No.: US 10,478,117 B2
(45) Date of Patent: Nov. 19, 2019

(54) EARLY DETECTION OF REDUCED BONE FORMATION WITH AN NMR SCANNER

(71) Applicant: Ramot at Tel-Aviv University Ltd., Tel-Aviv (IL)

(72) Inventors: Uri Nevo, Kadima (IL); Itzhak Binderman, Tel-Aviv (IL); Yifat Sarda, Ramla (IL); Elad Bergman, Haifa (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/565,171

(22) PCT Filed: Apr. 7, 2016

(86) PCT No.: PCT/IL2016/050372
§ 371 (c)(1),
(2) Date: Oct. 9, 2017

(87) PCT Pub. No.: WO2016/162871
PCT Pub. Date: Oct. 13, 2016

(65) Prior Publication Data
US 2018/0110459 A1   Apr. 26, 2018

Related U.S. Application Data

(60) Provisional application No. 62/144,445, filed on Apr. 8, 2015.

(51) Int. Cl.
*A61B 5/05* (2006.01)
*A61B 5/00* (2006.01)
(Continued)

(52) U.S. Cl.
CPC .......... *A61B 5/4509* (2013.01); *A61B 5/0037* (2013.01); *A61B 5/055* (2013.01); *A61B 5/4504* (2013.01); *A61B 5/486* (2013.01); *A61B 5/4839* (2013.01); *A61B 5/4848* (2013.01); *A61B 5/4872* (2013.01); *A61B 5/7275* (2013.01);
(Continued)

(58) Field of Classification Search
CPC ....... A61B 5/00; A61B 5/4509; A61B 5/0037; A61B 5/4554
See application file for complete search history.

(56) References Cited

U.S. PATENT DOCUMENTS

2012/0323110 A1   12/2012   Blake et al.
2014/0072571 A1   3/2014   Urdea et al.

FOREIGN PATENT DOCUMENTS

WO   WO 2006/091091   8/2006
WO   WO 2016/162871   10/2016

OTHER PUBLICATIONS

Hwang et al (Magnetic resonance imaging of bone marrow in oncology, Part 1) (Year: 2007).*
(Continued)

*Primary Examiner* — Joel F Brutus

(57) ABSTRACT

A method for early detection of bone deficiency in a patient, comprising:
collecting NMR signals of a bone marrow volume in a bone of the patient having normal bone density levels which are not indicative of bone deficiency as indicated by X-ray; and
analyzing said collected NMR signals to detect at least a presence or absence of a preclinical stage of bone deficiency in said bone.

13 Claims, 10 Drawing Sheets

(51) Int. Cl.
*A61B 5/055* (2006.01)
*G01R 33/48* (2006.01)
*G01R 33/54* (2006.01)
*G01R 33/56* (2006.01)

(52) U.S. Cl.
CPC ....... *G01R 33/4812* (2013.01); *G01R 33/543* (2013.01); *G01R 33/5608* (2013.01); *A61B 2560/0431* (2013.01); *A61B 2576/00* (2013.01)

(56) References Cited

OTHER PUBLICATIONS

Daldrup-Link et al (MR imaging of therapy-induced changes of bone marrow) (Year: 2007).*
Ragab et al (Bone marrow edema syndromes of the hip: MRI features in different hip disorders) (Year: 2008).*
Bolan et al (Water—Fat MRI for Assessing Changes in Bone Marrow Composition Due to Radiation and Chemotherapy in Gynecologic Cancer Patients) (Year: 2013).*
International Search Report and the Written Opinion dated Aug. 4, 2016 From the International Searching Authority Re. Application No. PCT/IL2016/050372.
International Preliminary Report on Patentability dated Oct. 19, 2017 From the International Bureau of WIPO Re. Application No. PCT/IL2016/050372. (6 Pages).

Akune et al. "PPAR[Gamma] Insufficiency Enhances Osteogenesis Through Osteoblast Formation From Bone Marrow Progenitors", The Journal of Clinical Investigation, 113(6): 846-855, Mar. 2004.
Bergman et al. "An Estimation Method for Improved Extraction of the Decay Curve Signal From CPMG-Like Measurements With a Unilateral Scanner", Journal of Magnetic Resonance, 245: 87-93, Available Online May 22, 2014.
Bernabei et al. "Screening, Diagnosis and Treatment of Osteoporosis: A Brief Review", Clinical Cases in Mineral and Bone Metabolism, 11(3): 201-207, Sep.-Dec. 2014.
Hillel et al. "Monitoring of Cellular Changes in the Bone Marrow Following PTH (1-34) Treatment of OVX Rats Using a Portable Stray-Field NMR Scanner", Journal of Osteoporosis, 2017(Art. ID7910432): 1-10, May 30, 2017.
Sigmund et al. "In Vivo Imaging of DDIF Contrast in the Human Knee", University of Leipzig, Germany, Poster Abstracts, 10: 93, 2009.
Yoshioka et al. "Magnetic Resonance Imaging", Elsevier Health, Section 1: General Imaging Priciples, Chap.3: 34-48, 2003.
Supplementary European Search Report and the European Search Opinion dated Jan. 2, 2019 From the European Patent Office Re. Application No. 16776226.9. (9 Pages).
Vande Berg et al. "Classification and Detection of Bone Marrow Lesions With Magnetic Resonance Imaging", Skeletal Radiology, XP055524996, 27(10): 529-545, Published Online Oct. 29, 1998. Figs.7A-7C.

* cited by examiner

EARLY DETECTION OF REDUCED BONE FORMATION WITH AN NMR SCANNER

RELATED APPLICATIONS

This application is a National Phase of PCT Patent Application No. PCT/IL2016/050372 having International filing date of Apr. 7, 2016, which claims the benefit of priority under 35 USC § 119(e) of U.S. Provisional Patent Application No. 62/144,445 filed on Apr. 8, 2015. The contents of the above applications are all incorporated by reference as if fully set forth herein in their entirety.

FIELD AND BACKGROUND OF THE INVENTION

The present invention, in some embodiments thereof, relates to characterizing bone tissue using NMR measurements, and, more particularly, but not exclusively, to detecting changes associated with Osteoporosis and/or Osteopenia.

Akune et al, "PPARγ insufficiency enhances osteogenesis through osteoblast formation in bone marrow progenitors," Journal of Clinical Investigation 113, 846-855 (2004), investigated the role of PPARγ, a key regulator of adipocyte differentiation, in bone metabolism.

Bergman et al, "An estimation method for improved extraction of the decay curve signal from CPMG-like measurements with a unilateral scanner," Journal of Magnetic Resonance 245, 87-93 (2014), presents a statistical signal-processing method that can improve the sensitivity of a CPMG-like sequence for measurements of transverse-relaxation with unilateral scanners, improving the extraction of the decay curve from the noisy data.

U.S. Patent Application Publication 2012/0323110 to Blake et al, relates to an MRI scan, and the resultant signal is used to give parameters that are employed to ascertain connectivity of trabeculae in the bone of the patient and volumetric trabecular density of the bone.

Sigmund et al, "In vivo imaging of DDIF contrast in the Human Knee," presented at Magnetic Resonance of Porous Media (MRPM), 2008, published in Poster Abstracts 10:93, 2009, relates to in vivo DDIF contrast results.

Published PCT patent application WO 2006/091091 to Van Nesselrooij et al describes a method for predicting the responsiveness to vitamin D/calcium therapy in an osteoporotic subject making use of a difference profile in NMR spectra of metabolites in a body fluid.

Yoshioka et al, "Magnetic Resonance Imaging," Chapter 3, p. 34-48, in Section 1, "General Imaging Principles," Elsevier Health, 2003, on pages 43-44, describes an indirect measure to assess the properties of trabecular bone often termed relaxometry or quantitative magnetic resonance (QMR).

Additional background art includes Cohen et al, "Teriparatide for idiopathic osteoporosis in premenopausal women: a pilot study," J Clin Endocrinol Metab. 2013 May; 98(5):1971-81. doi: 10.1210/jc.2013-1172. Epub 2013 Mar. 29; Yang et al, "Influences of teriparatide administration on marrow fat content in postmenopausal osteopenic women using MR spectroscopy," Climacteric. 2016 Jan. 8: 1-7. [Epub ahead of print]; Rickard et al, "Intermittent treatment with parathyroid hormone (PTH) as well as a non-peptide small molecule agonist of the PTH1 receptor inhibits adipocyte differentiation in human bone marrow stromal cells," Bone 2006 December; 39(6):1361-72. Epub 2006 Aug. 10; Singhal et al, "Regional fat depots and their relationship to bone density and microarchitecture in young oligo-amenorrheic athletes," Bone 2015 August; 77:83-90. doi: 10.1016/j.bone.2015.04.005. Epub 2015 Apr. 10; Müller-Bierl et al, "Cylinders or walls? A new computational model to estimate the MR transverse relaxation rate dependence on trabecular bone architecture," MAGMA. 2014 August; 27(4):349-61. doi: 10.1007/s10334-013-0402-7. Epub 2013 Sep.6. Erratum in: MAGMA. 2014 October; 27(5):465; Syed et al, "Effects of estrogen therapy on bone marrow adipocytes in postmenopausal osteoporotic women," Osteoporos Int. 2008; 19(9):1323-30; and Limonard et al, "Short-Term Effect of Estrogen on Human Bone Marrow Fat," J Bone Miner Res. 2015; 30(11):2058-66.

SUMMARY OF THE INVENTION

An aspect of some embodiments of the invention concerns a method for using NMR measurements to detect changes in the cellular composition of bone marrow that are likely to lead to osteoporosis or osteopenia, even before clinical indications of those conditions are apparent.

According to an aspect of some embodiments of the invention, there is provided a method for early detection of Osteoporosis or Osteopenia, comprising: collecting NMR signals of a bone marrow volume in a bone having normal bone density levels which are not indicative of Osteoporosis or Osteopenia as indicated by X-ray; and analyzing the collected NMR signals to detect a preclinical stage of Osteoporosis or Osteopenia in the bone. According to some embodiments of the invention, the analyzing comprises extracting, from the collected NMR signals, at least one parameter out of: T1 relaxation time, T2 and/or T2* relaxation time, and apparent diffusion coefficient. According to some embodiments of the invention, the analyzing comprises estimating adipose tissue content in the bone marrow volume indicative of Osteoporosis or Osteopenia. According to some embodiments of the invention, the adipose tissue content comprises at least one of a volume fraction of adipocytes and a population of adipocytes in the bone marrow volume. According to some embodiments of the invention, the method is performed without applying imaging pulses to the bone marrow volume. According to some embodiments of the invention, the analyzing comprises determining an increase in adipose tissue content based on a descending trend in T1 relaxation time. According to some embodiments of the invention, the analyzing comprises determining an increase in adipose tissue content based on a descending trend in ADC. According to some embodiments of the invention, a ratio between T1 and T2 and/or a ratio between T1 and T2* is indicative of changes in adipose tissue content. According to some embodiments of the invention, the collecting comprises scanning the bone marrow volume at least at two different time points, the time points being at least 6 weeks apart from each other.

According to some embodiments of the invention, the analyzing at the second time point provides feedback on a treatment prescribed to the patient. According to some embodiments of the invention, the second time point is performed before changes in cortical bone tissue in response to the treatment can be detected using X-ray.

According to some embodiments of the invention, the treatment is in the form of one or more administration of pharmaceutical agents, a dietary change, a change in physical activity. According to some embodiments of the invention, the method further comprises performing a scout scan of the bone to locate the bone marrow volume. According to some embodiments of the invention, the scout scan produces a depth profile of the bone. According to some embodiments of the invention, the bone marrow volume is located at respective center of the bone marrow cavity of the bone.

According to some embodiments of the invention, the bone marrow volume is between 10 micrometer^3-10 cm^3. According to some embodiments of the invention, the analyzing comprises at least one of a one dimensional or multi dimensional analysis of one or more of T1 relaxation time, T2 and/or T2* relaxation time, ADC extracted from the collected NMR signals. According to some embodiments of the invention, the method further comprises selecting patients for screening, the selected patients including patients which do not exhibit BMD levels indicative of Osteoporosis or Osteopenia.

According to an aspect of some embodiments of the invention, there is provided a method for estimating adipose tissue content, comprising: collecting NMR signals of a bone marrow volume in a bone using a stray field, non-homogenous NMR scanner; analyzing the signals to estimate adipose tissue content in the bone marrow volume. According to some embodiments of the invention, the method further comprises determining a preclinical stage of Osteoporosis or Osteopenia based on the adipose tissue content. According to some embodiments of the invention, the method comprises extracting, from the collected NMR signals, at least one parameter out of: T1 relaxation time, T2 and/or T2* relaxation time, apparent diffusion coefficient, the at least one parameter indicative of the adipose tissue content.

According to an aspect of some embodiments of the invention, there is provided a portable scanner device for early detection of Osteoporosis or Osteopenia, comprising: a magnet or magnetic field generator configured for applying a static stray magnetic field to a bone marrow volume in a bone having normal bone density levels; a module configured for generating excitation pulses and collecting NMR signals of the bone marrow volume; a processor configured for analyzing the collected NMR signals to detect a preclinical stage of Osteoporosis or Osteopenia in the bone.

According to some embodiments of the invention, the processor is configured to estimate adipose tissue content in the bone marrow volume. According to some embodiments of the invention, the device is configured as a hand held device, positionable externally to a patient. According to some embodiments of the invention, the device is configured as a table top device suitable for use at a physician's clinic.

According to some embodiments of the invention, the device is dimensioned to scan a bone marrow volume between 10 micrometer^3-10 cm^3. According to some embodiments of the invention, parameters of the applied excitation pulses are selected in accordance with the stray field generated by the magnet or magnetic field generator.

According to some embodiments of the invention, the magnet or magnetic field generator is configured for applying a static stray magnetic field between 0.1 Tesla to 1 Tesla to the bone marrow volume being scanned. According to some embodiments of the invention, the module is configured for generating the excitation pulses according to a selected characterization of the bone marrow volume. According to some embodiments of the invention, the module is configured for generating the excitation pulses according to at least one of a location of the bone marrow volume, and a size of the bone marrow volume. According to some embodiments of the invention, the device further comprises a user interface configured for receiving input parameters from a user. According to some embodiments of the invention, the input parameters include a selected characterization of the bone marrow volume. According to some embodiments of the invention, the user interface comprises a display for displaying results of the analyzing indicative of a condition of the bone.

According to an aspect of some embodiments of the invention, there is provided a method of non-invasive scanning of a bone marrow volume to detect a preclinical stage of Osteoporosis or Osteopenia in a patient, comprising providing a portable NMR scanner device; positioning the scanner device at a location of a bone intended for scanning, externally to the patient; activating the scanner device to collect NMR signals of the bone marrow volume; analyzing the collected signals to detect a preclinical stage of Osteoporosis or Osteopenia.

There is thus provided, in accordance with an exemplary embodiment of the invention, a method for early detection of bone deficiency in a patient, comprising:

collecting NMR signals of a bone marrow volume in a bone of the patient having normal bone density levels which are not indicative of bone deficiency as indicated by X-ray; and analyzing said collected NMR signals to detect at least a presence or absence of a preclinical stage of bone deficiency in said bone.

Optionally, the method comprises selecting a treatment for the patient, based on results of the analyzing, for treating bone deficiency.

Optionally, said analyzing comprises:

estimating adipose tissue content in said bone marrow volume; and determining if the adipose tissue content is indicative of bone deficiency.

Optionally, the method also comprising treating the patient between the two time points with a treatment for the pre-clinical stage of bone deficiency, wherein said analyzing at said second time point provides feedback on the treatment.

Optionally, the method further comprises selecting patients for screening, said selected patients including patients which do not exhibit BMD levels indicative of bone deficiency.

Optionally, the method further comprises determining a preclinical stage of bone deficiency based on said adipose tissue content.

There is further provided, in accordance with an exemplary embodiment of the invention, a scanner device for early detection of bone deficiency, comprising:

a portable magnet or magnetic field generator configured for applying a static stray magnetic field to a bone marrow volume in a bone having normal bone density levels;

an RF transmitter and receiver configured for generating excitation pulses and collecting NMR signals of said bone marrow volume; and a processor configured for analyzing said collected NMR signals to detect a preclinical stage of bone deficiency in said bone.

There is further provided, in accordance with an exemplary embodiment of the invention, a method of non-invasive scanning of a bone marrow volume to detect a preclinical stage of bone deficiency in a patient, comprising:

providing a portable NMR scanner device;

positioning the scanner device at a location of a bone intended for scanning, externally to the patient;

activating said scanner device to collect NMR signals of said bone marrow volume;

analyzing said collected signals to detect a preclinical stage of bone deficiency.

There is further provided, in accordance with an exemplary embodiment of the invention, a method of treating a patient with a pre-clinical stage of bone deficiency, comprising:

non-invasively determining that the patient has a pre-clinical stage of bone deficiency; and treating the patient for the pre-clinical stage of bone deficiency.

Optionally, determining that the patient has a pre-clinical stage of bone deficiency comprises non-invasively measuring adipose tissue content of bone marrow of the patient.

There is further provided, in accordance with an exemplary embodiment of the invention, a method of treating a patient having a pre-clinical stage of bone deficiency, comprising administering a drug from the group consisting of bisphosphonates, Denosumab, hormone replacement therapy drugs, raloxifene and other selective estrogen receptor modulators, and recombinant human PTH.

There is further provided, in accordance with an exemplary embodiment of the invention, a compound for use in the treatment of pre-clinical bone deficiency, from the group consisting of bisphosphonates, Denosumab, hormone replacement therapy drugs, raloxifene and other selective estrogen receptor modulators, and recombinant human PTH.

As will be appreciated by one skilled in the art, aspects of the present invention may be embodied as a system, method or computer program product.

Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 schematically shows a system for measuring NMR parameters in bone marrow, according to an exemplary embodiment of the invention;

DESCRIPTION OF SPECIFIC EMBODIMENTS OF THE INVENTION

Figure 1:
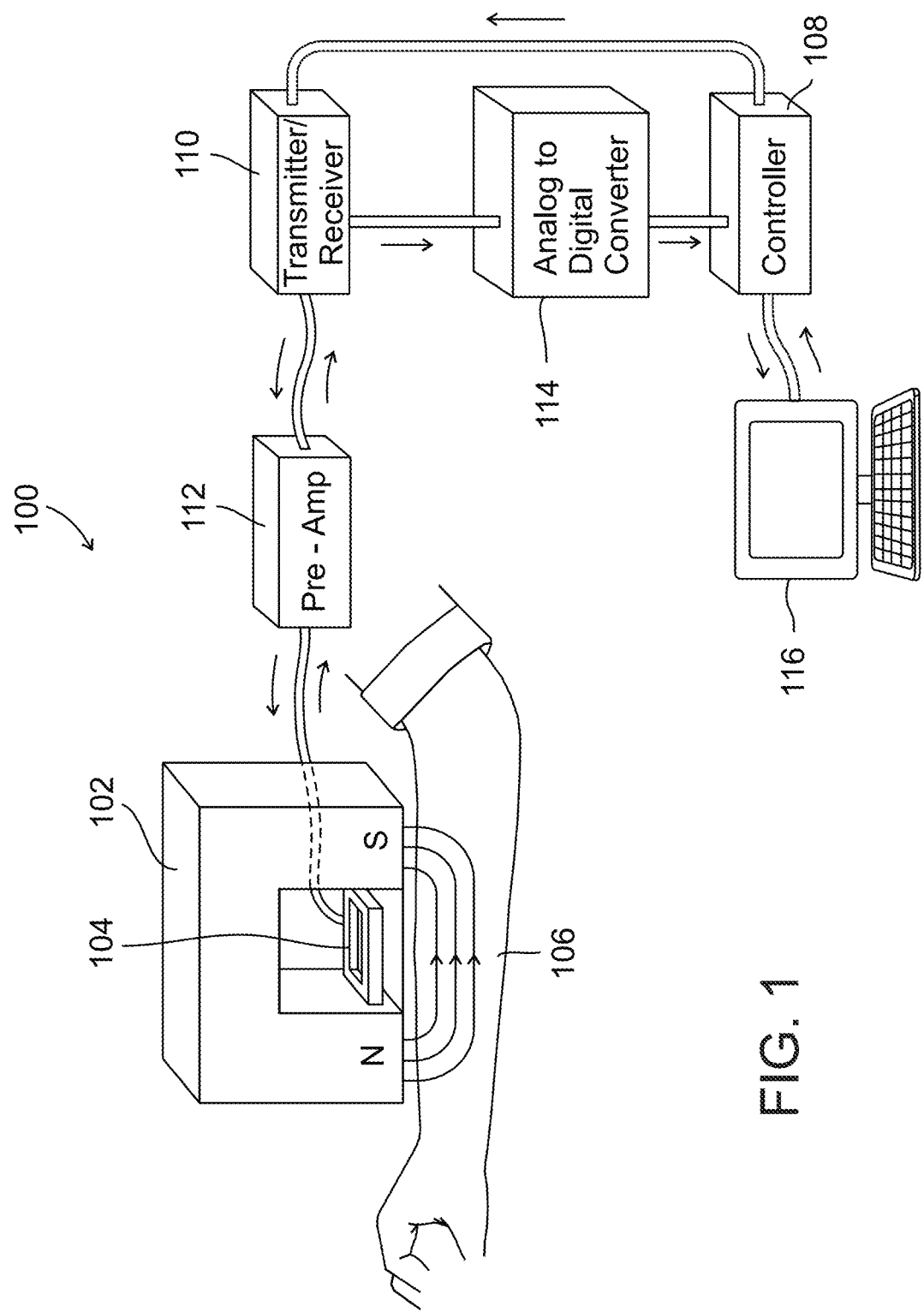

The present invention, in some embodiments thereof, relates to characterizing bone tissue, such as bone marrow, using NMR spectroscopy, and, more particularly, but not exclusively, to early detection of cellular changes indicative of reduced or even inhibited bone formation associated with Osteoporosis and/or Osteopenia. Patients exhibiting such changes are referred to herein as having a pre-clinical stage of osteoporosis or osteopenia.

More generally, patients exhibiting such changes are referred to herein as having a pre-clinical stage of bone deficiency, a term that may include other bone diseases characterized by reduced or inhibited bone formation. It should be understood that when "osteoporosis" or "osteopenia" is mentioned herein, optionally other diseases of bone deficiency are included as well.

An aspect of some embodiments of the invention relates to early detection of bone deficiency, such as Osteoporosis and/or Osteopenia, using Nuclear Magnetic Resonance (NMR) measurements of the bone marrow. Some embodiments relate to preventive screening and/or early detection of a bone condition that are performed before bone mineral density (BMD) levels indicative of Osteoporosis or Osteopenia can be detected in the bone using X-ray techniques, such as Dual-energy X-ray absorptiometry (DXA), or using MRI, for example using the MRI techniques described by Blake et al, or by Sigmund et al, referenced above. In some embodiments, the screening is performed to assess a human bone marrow condition. In some embodiments, patients selected for screening include patients having normal BMD levels, which are not indicative of Osteoporosis or Osteopenia. Optionally, normal BMD levels are determined according to common databases, and may differ between populations depending on one or more factors such as gender, age, physical condition and/or other factors.

Optionally, a clinical stage of osteoporosis or osteopenia refers to a patient for whom BMD levels are lower than an average value (for example, a mean or median or mode) for a relevant population for that patient, by at least 0.5 standard deviations, or at least 1 standard deviation, or at least 1.5 standard deviations, or at least 2 standard deviations, or a smaller, intermediate, or greater number of standard deviations. Alternatively, a clinical stage of osteoporosis or osteopenia refers to a patient whose BMD level has decreased by more than a certain amount compared to a baseline measurement of BMD made of the patient at a time when the patient was assumed not to have bone deficiency, for example a measurement made of the patient shortly before menopause. Optionally, in this case as well, the amount of decrease in BMD, necessary for the patient to be considered to have clinical osteoporosis or osteopenia, is based on the standard deviation of BMD for a relevant population, for example 0.5 or 1 or 1.5 or 2 times the standard deviation, or a smaller, intermediate, or greater number. It should be noted that the BMD for a given patient, in the absence of bone deficiency, may be expected to vary over time by less than a standard deviation of BMD for a population, so even a change by a fraction of a standard deviation may be clinically significant.

Similarly, the minimum changes in bone, or in cortical bone, that can be detected by x-ray, may be considered to be the changes that cause the BMD to change by 0.2, 0.5, 1, 1.5, or 2 times the standard deviation in BMD for a relevant population, or a smaller, intermediate or greater number of standard deviations.

In some embodiments of the invention, the screened patients, who may have a risk factor for developing osteoporosis or osteopenia, are prescribed treatments to prevent osteoporosis or osteopenia, based on the results of the screening. The risk factor may be based on age or gender, for example menopausal women, or may be based on use of a drug whose known side effects include osteoporosis or osteopenia, or may be based on exposure to environmental factors believed to have such an effect, or may be based on having a medical condition that increases the risk for osteoporosis or osteopenia. Optionally, the treatments are prescribed even for patients for whom the NMR measurements of bone marrow do not show any signs of pre-clinical osteoporosis or osteopenia, for example because they have a risk factor. But different treatments, for example more aggressive treatments, are optionally prescribed for the patients who do show signs of pre-clinical osteoporosis or osteopenia, according to the NMR measurements. Optionally, the NMR measurements of the bone marrow are repeated after treatment has continued for a period of time, and they are used to monitor the treatments, and if necessary to change the parameters of treatment, for example the dosage of a drug, or to keep the parameters of treatment unchanged, or to discontinue the treatment. The change or lack of change in the parameters of the treatment, or the decision to continue or discontinue the treatment, may depend, for example, on whether the NMR measurements show relevant NMR parameters of the bone marrow to be unchanged, or better or worse, and/or on whether they change as much as expected, or more than expected, or less than expected, or in the same direction or in a different direction than expected.

In some embodiments, a scout scan is performed to produce a depth profile of the bone, in order to locate a selected region of interest for scanning, such as a volume of bone marrow within the bone marrow cavity region. In an example, a bone marrow tissue volume at a depth between 0.5 cm to 5 cm from a surface of the skin is selected as the region of interest. In some embodiments, a size of the scanned tissue volume is 10, $10^2$, $10^3$, $10^4$, $10^5$, or $10^6$ micrometer^3, or $10^{-2}$, $10^{-1}$, 1, or 10 mm$^3$, or 0.1, 1, or 10 cm^3, or smaller, intermediate, or greater sizes.

In some embodiments, excitation pulses are applied to the selected tissue volume. Optionally, one or more parameters of the applied pulses (such as frequency, intensity, duration) are tailored according one or more of the type of tissue in the selected tissue volume, a location (e.g. depth) of the tissue volume, the type of characterization intended to be achieved by the scanning.

In some embodiments, the returning signals are collected and deterioration of the received NMR signals, in terms of T1 relaxation time and/or T2 relaxation time and/or T2* relaxation time, is assessed. In some embodiments, an apparent diffusion coefficient (ADC) of the scanned tissue is estimated. In some embodiments, the extracted parameters (e.g. T1, T2, T2* and/or ADC) are analyzed in order to arrive at an estimation of a current condition of the bone. In some embodiments, T2* (effective T2 of T2eff) is extracted.

As referred to herein, T2 may include a time constant for the decay of transverse magnetization arising from natural interactions at the atomic or molecular levels; T2* (effective T2 or T2eff) may include the observed or effective time constant for the decay of transverse magnetization, whereby a difference of T2* from T2 is a result of inhomogeneities in the main magnetic field; T1 may include the time constant for regrowth of longitudinal magnetization. Additionally or alternatively, the terms T1, T2 and T2* may be defined according to, but not limited to, other relaxation time definitions known in the art.

In some embodiments, an ascending trend or a descending trend of a relaxation parameter measured over time is indicative of cellular changes, such as a rise in adipose tissue content, which has been shown to be associated with early stages of a reduction in bone formation. In some embodiments, a population of osteoblast cells and/or a change in the osteoblast cell population is estimated. In some embodiments, a population and/or a change in the population of mesenchymal stem cells, the precursors of osteoblasts, is estimated. Optionally, as osteoblast cells take a roll in the bone synthesis process, the population of osteoblasts and/or the population of mesenchymal stem cells and/or changes in one or both of these populations may provide an early indication for a present or future reduction in bone formation.

As referred to herein, a "preclinical stage" and/or "early stage" may include a bone condition preceding clinical manifestations associated with Osteoporosis and/or Osteopenia. In some embodiments, the preclinical and/or early stage bone condition comprises an imbalance between bone resorption and bone formation processes. In some embodiments, the preclinical and/or early stage bone condition comprises a stage in which no physiological change has yet occurred and/or is not yet detectable in the trabecular and/or cortical bone tissues, such as weakening of the tissue and/or appearance of microcracks. In some embodiments, the preclinical and/or early stage bone condition comprises a stage in which changes in bone density and/or bone mass have not yet occurred and/or are not yet detectable. In some embodiments, the preclinical and/or early stage bone condition comprises a stage in which an altering of bone proteins and/or other biochemical markers (such as bone collagen breakdown) has not yet occurred and/or is not yet detectable. In some embodiments, the preclinical and/or early stage bone condition comprises a stage in which fragility fractures are not yet present in the bone. In some embodiments, the preclinical stage comprises the existence of physiological phenomena that is a precursor of future development of a disease.

As used herein, "adipose tissue content indicative of bone deficiency," and similar phrases, may refer to a measure of adipose tissue content, such as volume fraction of adipocytes, that is higher than a mean value for a relevant population, by a certain number of standard deviations for the population, for example 0.5, 1, 1.5 or 2 standard deviations, or by a certain percent increase, for example 3%, 5%, 10%, 20%, or 30%, or by smaller, intermediate or greater values. Optionally, instead of using the mean value for the population, an earlier measured baseline value for the patient is used, for example a baseline value measured at a time when the patient is assumed not to have any bone deficiency, for example before menopause. Using an earlier measured baseline value for that patient has the potential advantage that, in the absence of bone disease, the value of adipose tissue content for a given patient may be expected to vary much less over time than the standard deviation for the population, so even a small change may be a significant indication of pre-clinical bone deficiency. Changes in adipose tissue content of this magnitude may also be considered indicative of a worsening of bone deficiency, possibly indicating that a treatment is not working adequately, or of an improvement in bone deficiency, possibly indicating that a treatment is working well.

In some cases, parameters such as the ADC measure, T1 relaxation time and/or T2 and/or T2* relaxation time complement one another, for example, a descending trend of T1 may be accompanied by an ascending trend of T2 and/or T2*. A potential advantage of a complementary relationship between the measured parameters may include increasing a sensitivity of detection of cellular content and/or changes thereof.

In some embodiments, a change in T1, T2, T2*, ADC, or of a ratio or another combination of these parameters, is considered indicative of increased adipose tissue content, and hence indicative of bone deficiency, if it differs from a mean value of a relevant population by a certain number of standard deviations for the population, for for example 0.5, 1, 1.5 or 2 standard deviations, or by a certain percent increase, for example 2%, 3%, 5%, 10%, or 20%, or by smaller, intermediate or greater values. Optionally, instead of using the mean value for the population, an earlier measured baseline value for the patient is used, for example a baseline value measured at a time when the patient is assumed not to have any bone deficiency, for example before menopause. Using an earlier measured baseline value for that patient has the potential advantage that, in the absence of bone disease, the value of these parameters for a given patient may be expected to vary much less over time than the standard deviation for the population, so even a small change may be a significant indication of pre-clinical bone deficiency. Changes in these parameters of this magnitude may also be considered indicative of a worsening of bone deficiency, possibly indicating that a treatment is not working adequately, or of an improvement in bone deficiency, possibly indicating that a treatment is working well.

In some embodiments, scanning is performed every 1 month, every 3 months, every 6 months, every year, or intermediate, longer or shorter time ranges to assess a condition of the bone tissue, for example to assess a trend in bone formation, such as a reduction in the rate of bone formation or inhibition of bone formation. Optionally, scanning is performed before and/or during and/or following treatment of the patient, including one or more, for example, administering of medicine, a dietary change, and/or a change in physical activity. In some embodiments, scanning is performed to provide feedback on the treatment administered to the patient.

In some embodiments, cellular changes (e.g. a rise in the ratio between a population of osteoblasts and a population of adipocytes) in bone marrow in response to the treatment are observed before any changes can be observed in trabecular and/or cortical bone tissue. In an example, cellular changes in the bone marrow in response to medication can be detected by scanning the bone at 1-2 months after initial administration of the medication, while changes in the cortical bone tissue (e.g. changes in the bone density) in response to the a similar treatment can be observed only about 9 months or longer time periods after initial administration of the medication (for example by measuring bone mineral density, optionally using Dual-energy X-ray absorptiometry (DXA) and/or other techniques known in the art.).

An aspect of some embodiments relates to scanning of bone tissue to estimate cellular content and/or changes in cellular population. In some embodiments, scanning is performed without applying imaging pulses. Alternatively, imaging pulses are applied. Some embodiments of the invention involve the early detection of bone formation reduction or inhibition, as indicated for example by differentiation of bone marrow mesenchymal stem cells into adipocytes at the expense of osteoblasts.

In some embodiments, estimation of cellular changes includes estimating a volume fraction of adipocytes and/or a volume fraction of osteoblasts. Certain values (e.g. absolute values) and/or changes in the values of the estimated cellular volume fractions may be a precursor of bone loss processes. In some embodiments, the estimated cellular changes are associated with over expression of Peroxisome proliferator-activated receptor gamma (PPAR-γ), which is known to regulate adipocyte differentiation. Optionally, scanning is performed to estimate expression levels of PPAR-γ. In some embodiments, a treatment and/or additional diagnosis is selected based on the estimated expression level of PPAR-γ. In some embodiments, effects of PPAR-γ on regulation of bone metabolism for example as described in Akune T, et al, J. Clin. Invest. 113:846-855 (2004). doi:10.1172/JCI200419900, ("PPAR-γ insufficiency enhances osteogenesis through osteoblast formation from bone marrow progenitors") may be estimated using methods and/or devices described herein.

In some embodiments, an adipocyte content of the scanned tissue is estimated, without providing an indication of whether a disease has developed or is predicted to develop in the bone.

In some embodiments, more than one change in the cellular content is estimated at a single scanning session of the bone. In an example, a population (or a change in population) of osteopregenitors is estimated in addition to a population (or a change in population) of adipocytes.

An aspect of some embodiments relates to scanning bone tissue for early detection of Osteoporosis or Osteopenia using a stray field, non-homogenous portable NMR scanner.

In some embodiments, the scanner is configured as a compact, optionally hand held device. In some embodiments, the scanner is configured as table top device suitable for use at a physician's clinic. The scanner may be carried on a wheelable cart, attached to a moveable lever, and/or any other configurations which will provide for positioning the scanner relative to the scanned body portion, and/or positioning the scanned body portion relative to the scanner. In some embodiments, the scanner weighs less than 5 Kg, less than 10 Kg, less than 1 Kg, less than 0.5 Kg, or intermediate, higher or smaller values.

In some embodiments of the invention, an NMR scanner referred to herein as "non-homogeneous," "stray field" or "unilateral," has a scanned volume located outside the scanner. Additionally or alternatively, such a scanner has a static magnetic field whose scale length, defined for example as ratio of field magnitude to field gradient magnitude, is less than 10 times the greatest diameter of the scanner, or less than 5 times, less than 2 times, less than 1 time, less than 0.5 times, or less than 0.2 times the greatest diameter of the scanner, or less than 10, 5, 2, 1, 0.5, or 0.2 times the greatest dimension of the volume that can be scanned at a given position of the scanner. In typical large bore-type MRI scanners, by contrast, the scale length of the static magnetic field is typically orders of magnitude greater than the size of the scanner, or the size of the scanned volume.

In some embodiments, the scanner is placed against the patient's body, externally to the skin at a location of the targeted bone. Additionally or alternatively, scanning involves positioning the tested organ relative to the scanner (for example placing the patient's arm within a designated cavity of the scanner). Additionally or alternatively, in some embodiments, a bone or an extracted bone sample is placed on a surface of the scanner.

In some embodiments, the device is dimensioned to scan a bone tissue volume between 10 micrometer^3-10 cm^3. In some embodiments, the device comprises a magnet or magnetic field generator configured for applying a static stray magnetic field of, for example, between 0.1-1 Tesla, such as 0.3 Tesla, 0.6 Tesla, 0.9 Tesla or intermediate, higher or lower values.

In some embodiments, the device comprises a module configured for generating excitation pulses and collecting NMR signals. In some embodiments, the scanning profile is selected according to type and/or dimensions and/or location of the selected region of interest in the bone, such as a bone marrow volume at the center of the bone marrow cavity. In some embodiments, one or more parameters such as intensity, frequency, duration and/or other parameters of the applied excitation pulses are selected according to one or more of the type of tissue being scanned, the size of the volume of tissue being scanned, the tissue characterizing measures intended to be achieved by the scanning.

In some embodiments, the device comprises a memory for storing current and/or previous scanning results.

In some embodiments, the device comprises a processor which is configured to automatically extract parameters such as T1, T2, T2*, and/or ADC from the returning signals, by applying a signal processing algorithm. Optionally, an estimation algorithm is applied to reduce noise. In some embodiments, a one-dimensional and/or multidimensional analysis of one or more of the extracted parameters is performed. In some embodiments, the processor is configured to compare and/or perform calculations on the results of more than one scanning session, for example comparing previous scanning results (such as results obtained 1 month, 3 months, 1 year ago) with current scanning results.

In some embodiments, the device comprises a user interface configured to receive input from a user, such as scanning parameters, patient data, a selection of the type of tissue characterization required. In some embodiments, the user interface provides output to the user, for example, in some embodiments the device comprises a display on which information can be displayed to the user, such as a current scanning status, extracted parameters. In some embodiments, the displayed information includes estimations that were reached at based on the measured parameters, such as adipose tissue content, an indication of an early, preclinical stage of Osteoporosis or Osteopenia in the bone, feedback on treatment that was assigned to and/or provided to the patient (e.g. administering of pharmaceuticals, dietary change, a change in exercise and/or other lifestyle changes), and/or other indications. In some embodiments, the displayed information includes suggestions for future actions, such as the type of treatment that should be administered to the patient, dosage or changes thereof, statistics of the screened population and/or statistics of a specific patient, and/or other data which may assist the physician in determining future actions.

In some embodiments, methods and/or devices as described herein are useable in space medicine applications, for example for the monitoring of bone loss in astronauts.

Some embodiments of the invention relate to early detection of a reduction in bone formation. In some embodiments, bone formation inhibition is detected. In some cases, bone inhibition has a crucial effect on the prevention and treatment of diseases related to bone degeneration and/or reduced bone formation and/or bone resorption such as Osteoporosis. Reduced bone formation is, in some cases, caused by a disturbance in bone homeostasis leading to over differentiation of bone marrow mesenchymal stem cells (MSC) into adipocytes at the expense of osteoblasts. Such disturbances can cause a reduction in bone formation which leads to the development of well known bone diseases, including Osteopenia and Osteoporosis.

A potential advantage of a method for example as described herein may include noninvasive, early detection of this phenomenon. Current clinically approved methods use x-ray for the detection of bone mineral density (BMD), and may be effective only at a later stage of the disease, in which major damage to the bone is already present.

In some embodiments, a method for example as described herein detects alteration in the biochemical characteristics of the bone marrow, optionally at the initial evolution of the diseases. In some embodiments, detection is performed by NMR measurements using a portable stray field NMR scanner. In some embodiments, a depth-profile is applied to identify the middle of the bone marrow cavity region. In some embodiments, NMR methods which are suitable for inhomogeneous magnetic fields are applied to measure T2 and/or T2* relaxation time and/or T1 relaxation time and/or one or more diffusion coefficients. In some embodiments, a one-dimensional analysis and/or a multi-dimensional analysis are employed to detect a diseased bone, optionally at an early, preclinical stage of the disease.

Some embodiments of the invention relate to a portable, low cost NMR scanner that will be useable in clinics such as an endocrinologist clinic, orthopedics clinic, and/or other health practitioners and in medical centers, for preventive screening and for early detection of changes to the bone.

In some embodiments, first time changes in bone marrow content are detected using a unilateral, stray field NMR scanner. Optionally, the changes are detected prior to a detectable effect on the BMD. In some embodiments, profiling is performed to set the exact region of interest and the scan of the bone content with no imaging, by exploiting the strong spatial gradients of the magnetic field and without application of imaging gradient pulses. In some embodiments, pulse sequences that are specific to a stray field NMR scanner for this purpose are applied. In some embodiments, detection of T2 and/or T2* in very short echo times is performed. In some embodiments, a multidimensional analysis of T1, T2 and/or T2* and/or ADC is performed. In some embodiments, advanced signal processing algorithms are applied for the extraction of the relaxation times.

In some embodiments, variations in cellular populations are detected. Optionally, the variations are indicative of a reduction in bone formation at an early, preclinical stage. In some cases, cellular variations are associated with over expression of the PPARγ molecule, which is known to inhibit the bone formation path, while amplifying a positive feedback of preadipocytes to differentiate into marrow adipocytes. Future consequences of this effect may lead to bone diseases such as Osteopenia and Osteoporosis. In some cases, these cellular modifications in the bone marrow are reflected in changes in the biochemical characteristics of this tissue.

In some embodiments, a bone disease is detected at an early stage using an inhomogeneous NMR scanner. The term "inhomogeneous NMR scanner", as referred to herein, may include, but not limited to, a scanner in which the resulting bandwidth of a scanned macroscopic object cannot be reduced below hundreds and/or thousands of Hz. In some embodiments, a bone is placed on top and/or adjacent and/or within a defined cavity of the NMR scanner. In some embodiments, the scanner is a small, portable bench-top NMR scanner, characterized by a low and inhomogeneous scanner.

In some embodiments, a depth-profile scan is applied to identify the central part of the bone marrow cavity. In some embodiments, NMR methods which are specifically suitable to inhomogeneous magnetic fields and to measuring the apparent diffusion coefficient (ADC), T2 and/or T2* and/or T1 relaxation times are applied. In some embodiments, the analysis includes mono and/or bi-exponent fitting. In some embodiments, an estimation algorithm is applied to reduce noise before curve fitting. It is noted that previous studies performed using large, massive MRI/NMR devices with MRS technique showed a relation between fatty marrow content and its effect on T1, T2, T2* and ADC.

An aspect of some embodiments of the invention concerns non-invasively detecting a pre-clinical stage of bone deficiency in a patient, and treating the patient for the pre-clinical stage of bone deficiency, for example using any of the treatments described below under "Possible treatments for pre-clinical bone deficiency." Optionally, the pre-clinical stage of bone deficiency is detected by non-invasively measuring the adipose tissue content of the patient's bone marrow. Optionally, the adipose tissue content is measured by measuring one or more NMR parameters of the bone marrow, such as T1, T2, T2*, or ADC.

An aspect of some embodiments of the invention comprises a method of treating a patient having a pre-clinical state of bone deficiency, for example using any method used for clinical stages of osteoporosis or osteopenia, for example any of the drug treatments or other treatments listed below under "Possible treatments for pre-clinical bone deficiency." An aspect of some embodiments of the invention comprises a compound for use in the treatment of pre-clinical stage bone deficiency, from a group consisting of all compounds used to treat clinical stage osteoporosis or osteopenia, for example from a group consisting of bisphosphonates, Denosumab, hormone replacement therapy drugs, raloxifene and other selective estrogen receptor modulators, and recombinant human PTH. An aspect of some embodiments of the invention concerns the use of a compound in the group consisting of bisphosphonates, Denosumab, hormone replacement therapy drugs, raloxifene and other selective estrogen receptor modulators, and recombinant human PTH, in the manufacture of a medicament for the treatment of pre-clinical stage bone deficiency.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 schematically illustrates a system 100 for measuring NMR parameters in bone marrow, according to an exemplary embodiment of the invention. An NMR device comprises a magnet 102, and an RF transmitting and receiving coil 104, is positioned adjacent to a bone in a subject, for example a bone in an arm 106 of a human subject, to produce a static magnetic field and RF magnetic fields of desired strength in a part of the bone where measurements are being made. Optionally, separate RF transmitting and receiving coils are used, or there is more than one RF coil used for both transmitting and receiving. Optionally, as in the example shown, the NMR device is a unilateral NMR device, of relatively small size and optionally portable, that is used to make measurements on one side of the device, as opposed to a full-size NMR device in which all or a large part of the body of a human subject is positioned inside a bore. Alternatively, the NMR device is a full-sized NMR device, or a smaller NMR device with a bore large enough to place a limb of a human subject, for example. In unilateral NMR devices, and in other small NMR devices, the magnet is optionally a permanent magnet. Although higher and more uniform magnetic fields, for example 3 tesla fields, and consequently larger signal to noise ratio, can generally be obtained with the stronger static magnetic fields possible in the bore of an electromagnet, especially a superconducting magnet, it is often not possible or not practical to obtain such high magnetic fields using an electromagnet in a smaller NMR device, because the current densities would have to be too high. For such smaller devices, lower static magnetic fields, of 1 tesla or 0.5 tesla for example, may be obtained using permanent magnets.

It should be noted that magnet 102 and RF coil 104 are not necessarily drawn to scale with arm 106 in FIG. 1, and often the magnet and RF coil will be smaller than shown in FIG. 1, which can make them more portable, and can allow them to make measurements limited to a smaller volume of the bone of interest. The NMR device can be used for any kind of bone, in vivo or in vitro, and for non-human bones as well, for example the rat femur and tibia bones used in the experiments described below in the Examples section, and the size of the device may be different depending on what kind of bone it is being used for. For example, the device is optionally small enough to limit the volume where the measurement is being made to a desired part of the bone marrow. But the device is optionally large enough to allow measurements to be made, with sufficient sensitivity, at a desired distance beneath the skin of the subject, and over a large enough volume of bone marrow.

In NMR measurements, a static magnetic field is produced in a volume of interest, in this case a volume of bone marrow in a subject. The magnetic field magnetizes the nuclei of atoms with a non-zero spin, principally hydrogen ions in the case of medical NMR making measurements in body tissue, so that slightly more of them are aligned with the magnetic field than against the magnetic field. An RF pulse is then applied to the volume of interest, changing the magnetization of the nuclei to a direction perpendicular to the static magnetic field, or at least with a perpendicular component, and the nuclei then precess around the direction of the static magnetic field. One or more further RF pulses, with timing and phase depending on what NMR pulse sequence is being used, further manipulate the spins of the nuclei to produce echoes, which can be detected by the RF coils. Several relaxation times and other parameters of medical interest can be measured in the tissue using NMR, including T1, the characteristic time for the nuclei to regain their alignment along the static magnetic field; T2, the time for precessing nuclei to get out of phase due to characteristics of the tissue; T2*, or effective T2, the time for precessing nuclei to get out of phase due also to inhomogeneities in the static magnetic field; and ADC, the apparent diffusion coefficient of nuclei into and out of the region where the static and RF fields are present.

Further information on the strengths of static and RF magnetic fields used in NMR, on the many different known NMR pulses sequences and what they are useful for in medical NMR, and on possible configurations of magnets and RF coils in NMR devices, see any textbook or review article on NMR, for example Yoshioka et al, referenced above, and references therein. Information on unilateral NMR devices is also found, for example in Bergman et al, referenced above. The NMR MOUSE, a commercially available unilateral NMR device mentioned in Bergman et al, is an example of an NMR device suitable for use in system 100.

In system 100, a controller 108 controls the timing, shape, and phase of the pulses in the RF pulse sequence, which is produced by transmitter/receiver 110. Transmitter/receiver 110 transmits signals for the RF pulse sequence to pre-amplifier 112, which amplifies the signals to a desired level, and sends the amplified signals to RF coil 104, which produces the pulsed RF fields in the volume of interest of bone marrow in arm 106. RF coil 104 receives RF echo pulses from the bone marrow, which are amplified by pre-amplifier 112, and received by transmitter/receiver 110. Alternatively, a separate RF coil, a separate pre-amplifier, and/or a separate receiver, is used for receiving the RF echo pulses. Transmitter/receiver 110 optionally sends the amplified RF echo pulses to analog to digital converter 114, which optionally digitizes the signals. The digitized signals are then sent to controller 108, or to a separate computing device, which optionally records them, and analyzes them to extract parameters of interest, such as one or more of T1, T2, effective T2, and ADC. The signal analysis by controller 108 optionally includes one or more signal processing methods described by Bergman et al, cited above, for extracting NMR relaxation times from noisy NMR signals. Controller 108 optionally displays raw or processed signals, and/or NMR parameters or other results of the signal analysis, on a user interface device 116. Optionally user interface device 116 is also used to choose parameters of the NMR pulse sequence, and/or parameters of the NMR signal analysis. User interface device 116 includes, for example, a monitor, a keyboard, and a mouse.

Optionally, one or more of controller 108, transmitter/receiver 110, pre-amplifier 112, and analog to digital converter 114, are integrated together with magnet 102 and RF coil 104 in a single portable device, for example in a portable stray field NMR scanner. Alternatively, only magnet 102 and RF coil 104 are integrated into a portable device, and the other components are separate, for example connected to the RF coil and to each other by cables. Alternatively, magnet 102 and RF coil 104 are not portable.

Figure 2:
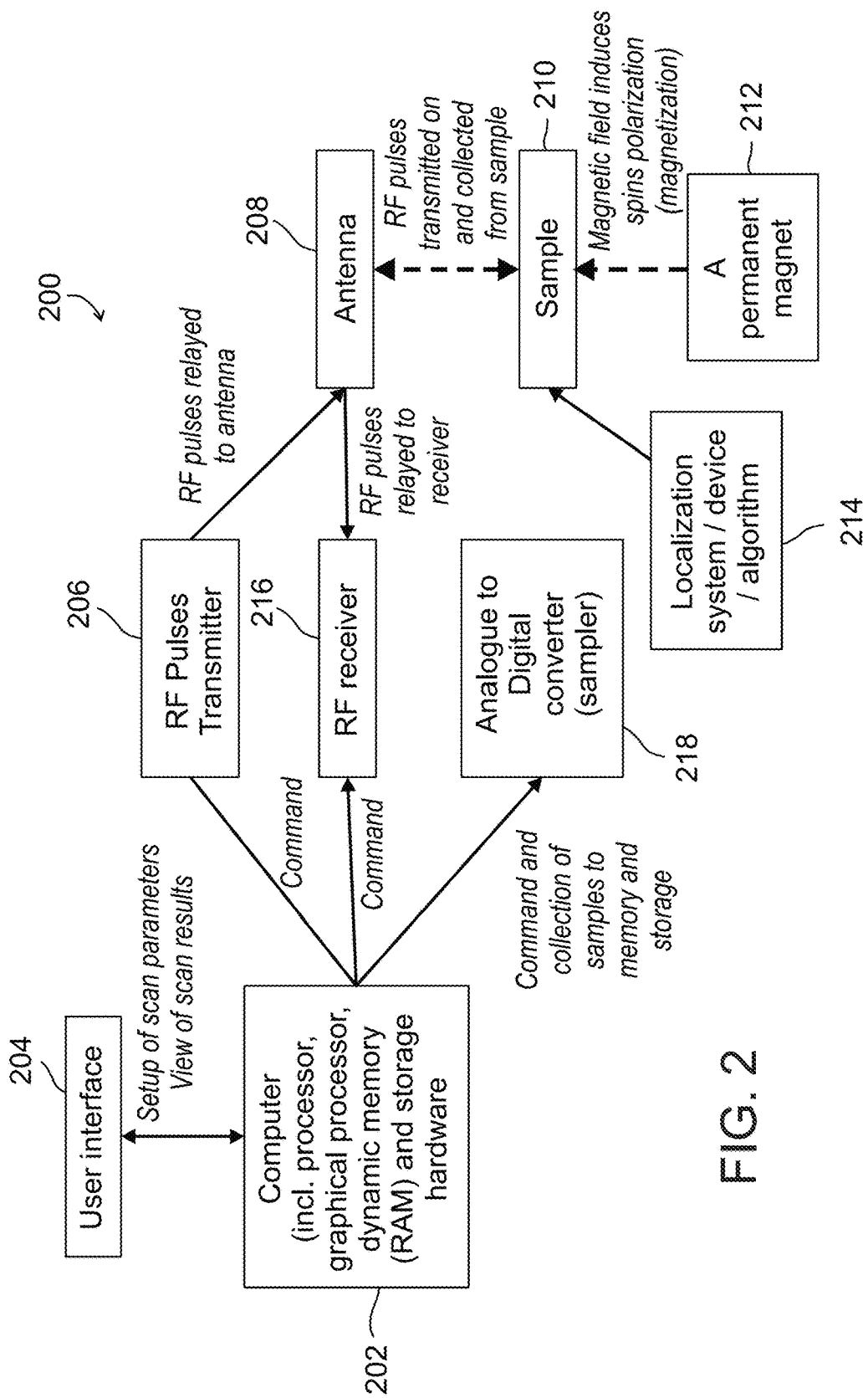
FIG. 2 is a block diagram for a system such as that shown in FIG. 1.

FIG. 2 shows a block diagram 200 of an NMR system such as system 100, suitable for measuring NMR parameters in bone marrow. A computer 202 controls the transmission of RF pulses and the collection and analysis of NMR signals from the resulting RF pulses. A user interface 204 is optionally used to control parameters used by computer 202, including parameters of the RF pulse sequence, and parameters of the signal processing and analysis. In particular, computer 202 controls RF transmitter 206, which transmits RF pulses to RF antenna 208, with shape, timing, and phase all optionally specified by computer 202. RF antenna 208, for example an RF coil as shown in FIG. 1, transmits the RF pulses to sample 210, a volume of bone marrow for which the NMR parameters are being measured. Permanent magnet 212, or another source of a static magnetic field, magnetizes sample 210, by polarizing the spins of nuclei in the sample, generally hydrogen nuclei, in the direction of the static magnetic field.

Localization system 214 controls for which slice or portion of sample 210 the NMR parameters are measured. Generally, NMR signals are only received from a portion of sample 210 for which the RF pulses have a frequency close enough to the precession frequency of the nuclei, which depends on the strength of the static magnetic field. Particularly for unilateral NMR devices, the static magnetic field may be quite non-uniform in the sample, so NMR signals may be received from only a relatively thin slice of the sample at a time. Localization system 214 controls the location of the slice for which NMR signals are received, either by moving the sample relative to the NMR device, for example moving one while the other is held in a fixed position, and/or by changing the RF frequency of the pulses. If the transmitter and RF antenna have a relatively narrow range of frequencies at which they operate well, then changing the position of the sample relative to the NMR device may be a better way to change the location of the slice for which NMR signals are received, than changing the RF frequency. Optionally localization system 214 is under the control of computer 202, and/or parameters used by localization system 214, for example the locations of one or more slices of sample 210 where NMR parameters are to be measured, are sent to localization system 214 by computer 202, optionally after the parameters are entered into computer 202 by a user through user interface 204. Different locations in the sample may give different information about the bone marrow. For example, as described below in Table 2 in the Examples section, differences in T2 seen between rats that were treated with parathyroid hormone after ovariectomies, and rats that were not treated, are greater in the peripheral zone of the bone marrow than in the central zone, and it may be preferable to measure NMR parameters in a peripheral part of the bone marrow. In other cases, including for the results shown in Table 1 and in FIGS. 8, 9A, and 9B, NMR parameters are measured in a central part of the bone marrow.

Figure 5:
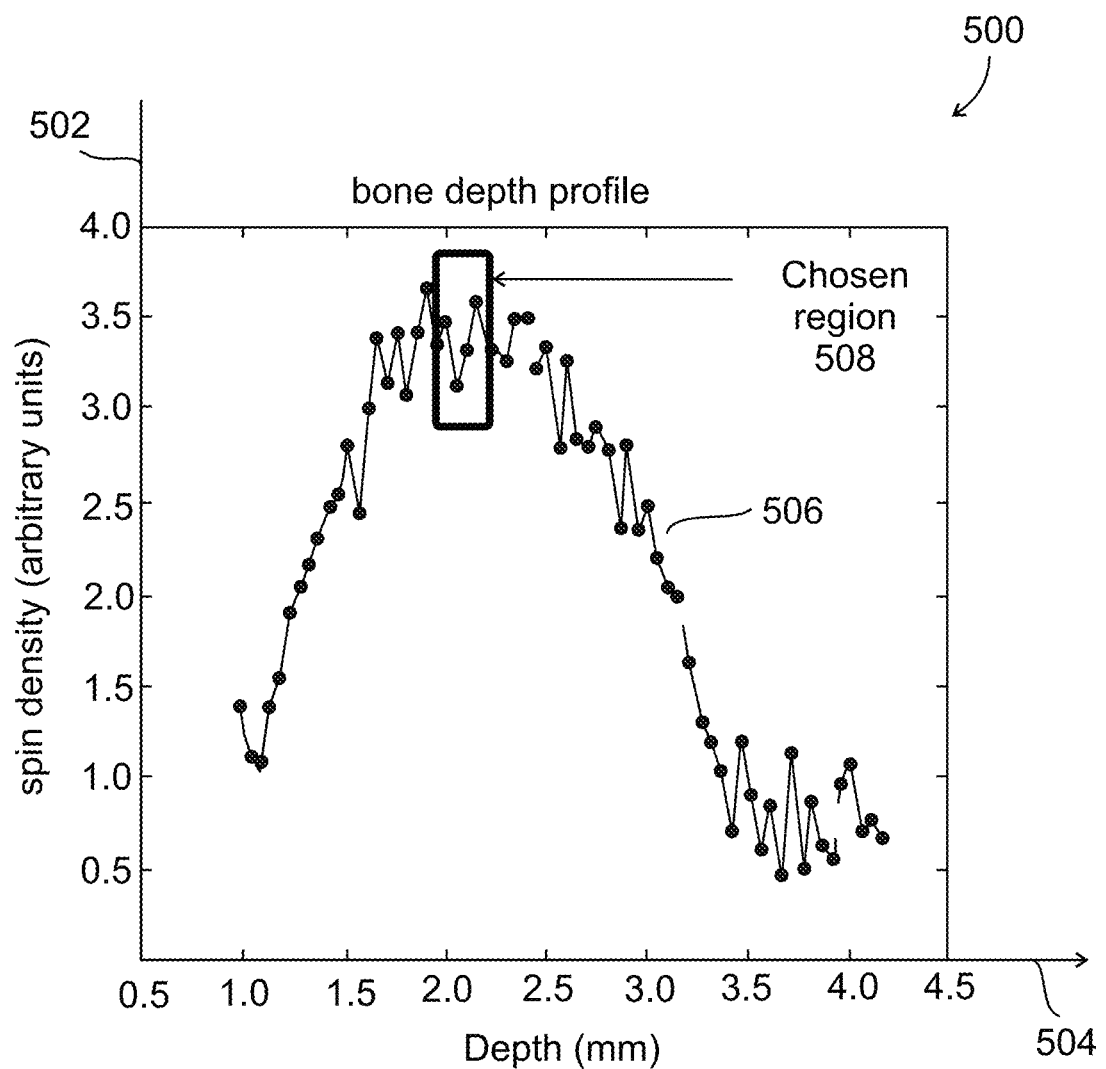
FIG. 5 is a plot of bone marrow density as a function of depth, showing a region in which NMR measurements were made, in the experiments outlined in FIG. 4.

A peripheral zone of the bone marrow is defined, for example, as a part of the bone marrow that is closer to a bone wall than to the center of the bone marrow, or less than 20% of the way from the wall to the center, or less than 30% of the way from the wall to the center, or less than 70% of the way from the wall to the center, or a greater or lesser or intermediate value. Alternatively, a peripheral zone is defined as a part of the bone marrow where the density as measured in an NMR scan, such as the density shown in FIG. 5, is less than 70% of the peak density, or less than 50% of the peak density, or less than 30% of the peak density, or a greater or lesser or intermediate value. The central zone of the bone marrow is optionally defined as the part of the bone marrow other than the peripheral zone, by any of these definitions.

Alternatively, particularly if a more traditional MRI device is used, with a relatively uniform static magnetic field in a bore, whether a full-sized device for a whole body scan or a smaller device for scanning one limb, an MRI image is made, using variable gradient magnetic fields produced by gradient coils, covering an extended volume of the bone marrow, instead of or in addition to using localization system 214 to measure NMR parameters at only one slice of sample 210 at a time, averaged over that slice. Although MRI images can also be made using unilateral NMR devices, with their relatively non-uniform static magnetic fields, the signal to noise ratio is such images is generally much lower than in images made using dedicated MRI devices with very uniform magnetic fields, and measuring NMR parameters averaged over a slice may provide more accurate values of the NMR parameters, and may be adequate for the purposes of evaluating whether the bone marrow shows signs of pre-clinical bone disease.

RF echo pulses emitted by sample 210, are received by RF antenna 208, or optionally by a different RF antenna than the antenna used for transmitting RF pulses, and relayed to a receiver 216, optionally part of transmitter 206, or alternatively a separate unit. Particularly if the same antenna is used for transmitting and receiving RF pulses, and/or if the same unit is used for amplifying them, it is potentially advantageous to receive RF echo pulses only at times when no RF pulses are being transmitted, and when any transients from the transmitted RF pulses have decayed away to a very low level, since typically the transmitted pulses have very much higher amplitude than the received pulses. To avoid damage to receiver 216, optionally it is turned off during times when RF pulses are being transmitted. Optionally, an amplified received signal from receiver 216 is sampled and/or converted from analog to digital form by an analog to digital converter 218, also optionally under the control of computer 202, and/or receiving operating parameters from computer 202.

Figure 3:
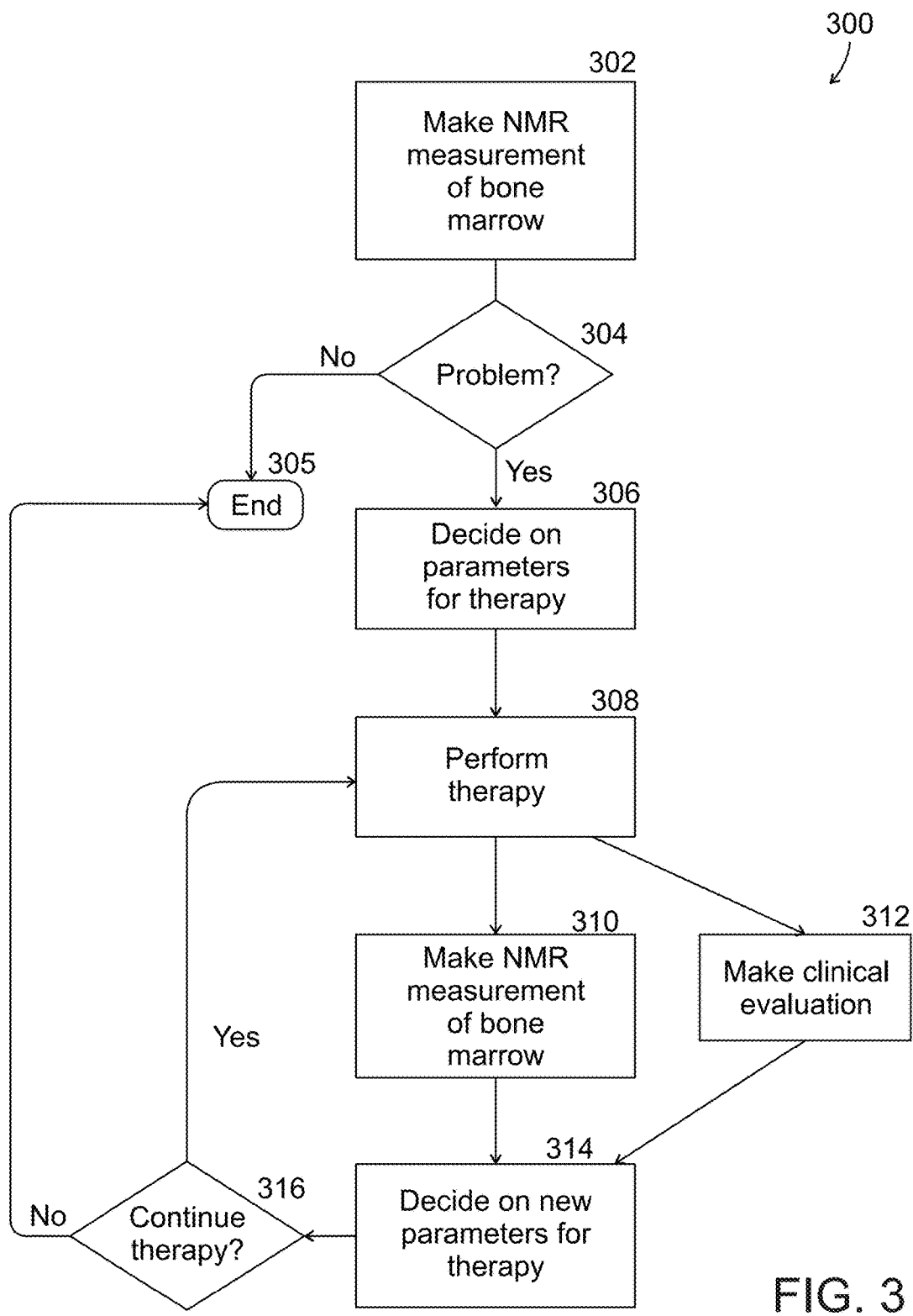
FIG. 3 is a flowchart for a method of adjusting treatment parameters of a patient based on NMR measurements of bone marrow, according to an exemplary embodiment of the invention.

The information on NMR parameters in bone marrow found using system 100 or the system described by block diagram 200 can be used in a number of different ways to help to diagnose or treat patients who may be in danger of suffering from osteoporosis or osteopenia. For example, FIG. 3 shows a flowchart 300 for a method of using NMR measurements of bone marrow to monitor the therapy used to treat or prevent osteoporosis or osteopenia, including in patients who do not yet show any clinical signs of osteoporosis or osteopenia. At 302, NMR measurements are made of bone marrow in the patient. Optionally, these measurements, which may be relatively easy and inexpensive to make if a small unilateral NMR device is used, are made for screening patients, for example menopausal women, or patients currently taking drugs that are known to sometimes cause osteoporosis or osteopenia as a side effect, or other patients considered to belong to risk groups for osteoporosis and osteopenia. At 304, a decision is made as to whether the NMR parameters measured at 302 indicate a likely problem. For example, the decision can be made based on whether parameters such as T1, T2, T2*, and ADC, or a change in one or more of these parameters since a previous measurement was made on the same patient, indicate that the patient's bone marrow has a larger than normal number of adipocytes, or an increasing number of adipocytes, which may indicate a pre-clinical stage of osteoporosis or osteopenia.

If no problem is indicated at 304, then no further action needs to be taken, and the method ends at 305, though the patient may be scheduled for further measurements of NMR parameters in bone marrow in the future. If a problem is indicated at 304, then at 306 is decision is made on parameters of therapy for treating the patient, for example with the goal of preventing the patient from progressing to clinical osteoporosis or osteopenia. The therapy optionally compromises treatment with a drug known to increase or maintain osteogenesis. Examples of such drugs are listed in the section titled "Possible treatments for pre-clinical osteoporosis and osteopenia," below. The parameters of therapy optionally include a dosage for such a drug. The parameters of therapy are optionally selected based on the NMR parameters measured at 302, as well as based on other factors such as the age and gender of the patient, other medical conditions the patient has or had in the past, and/or drugs or other therapy that the patient is receiving or has received for other medical conditions.

At 308, the therapy is performed according to the parameters chosen at 306, for example the patient is treated with the chosen drug, at a chosen dose, for chosen period of time, long enough to evaluate what effect the therapy is having on the patient's bone marrow. At 310, another NMR measurement is made of the patient's bone marrow. Optionally, a clinical evaluation is also made of the patient's condition, at 312, for example to determine if the patient is showing any clinical signs of osteoporosis or osteopenia, and/or to evaluate other medical conditions the patient may have, or other factors that may affect the choice of therapy. At 314, based on the new NMR measurements at 310, and optionally on the clinical evaluation made at 312, new parameters for therapy are chosen, for example a higher or lower dosage of a drug that was chosen for therapy at 306, or a different choice of drug. For example, the NMR parameters indicated that the patient's bone marrow has a higher level of adipocytes than before, or has not improved as much as expected, then the dosage of a drug may be raised, or a stronger drug may be chosen, or a different drug may be chosen that is more effective in some patients. If the NMR parameters indicated that the patient's bone marrow has improved even faster than expected, and/or if the clinical evaluation indicates other medical problems or side effects that may make it inadvisable for the patient to continue with the therapy using the same parameters, then the dosage of a drug may be decreased, or the therapy may be discontinued, and/or a different drug may be chosen that is less likely to cause the side effects, or is safer to use in that patient. Alternatively, if the NMR parameters found at 310, and the clinical evaluation at 312, indicate the patient's condition is progressing in a satisfactory way, then the new parameters for therapy chosen at 314 may be the same as the existing parameters.

At 316, if the decision was made at 314 to discontinue the therapy, then the method ends at 305. Otherwise, the therapy is performed again at 308, using the new parameters chosen at 314.

Results of Experiments

A method as described herein was tested ex-vivo on the femur and tibia bones past removal of ovaries (ovariectomy, OVX). Bones at 3.5 and 4.5 months post OVX showed a remarkable reduction in both the apparent diffusion coefficient (ADC) and T1 relaxation time, and an increase in the T2 relaxation time, compared to sham operated rats. Multidimensional analysis further demonstrated a clear discrimination of a diseased bone, at an early stage.

Figure 4:
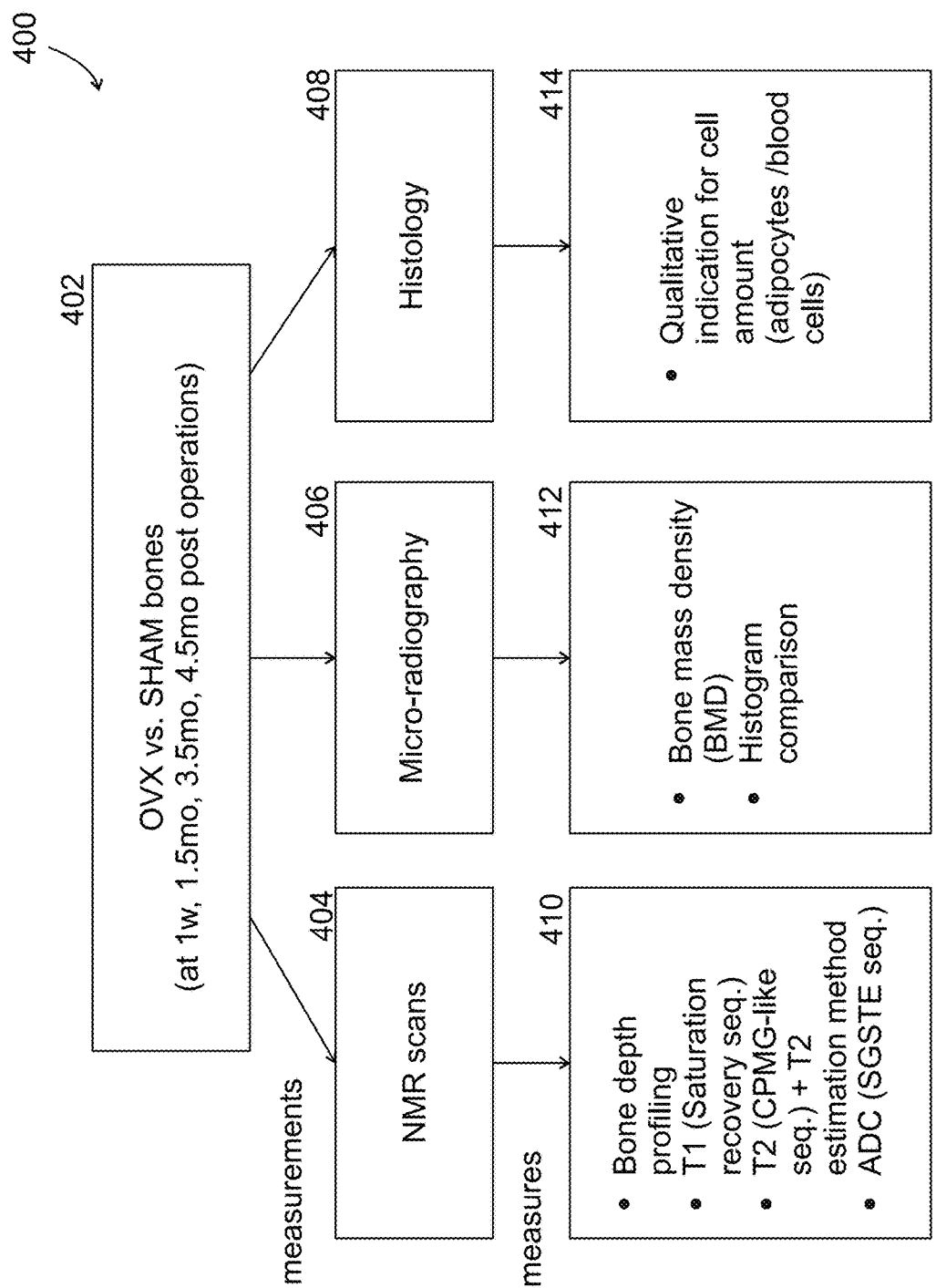
FIG. 4 is a chart outlining results of experiments, performed according to an embodiment of the invention, illustrating the effect of ovariectomies in rats on bone marrow, including effects on NMR parameters.

FIG. 4 shows a chart 400 outlining the experiments performed and the different measurements made on the OVX and sham operated rats. Box 402 summarizes the experimental protocol: Bones from OVX and sham operated rats were evaluated at 1 week, 1.5 months, 3.5 months, and 4.5 months after the operations. The most significant differences in NMR parameters for the OVX and sham operated rats were seen 3.5 and 4.5 months after the operations, and the results from those measurements are presented here.

The evaluations of the bones included NMR scans at 404, micro-radiography studies at 406, and histology studies at 408. The NMR scans included several kinds of measurements, listed at 410. Bone depth profiling was done, and was used to select a slice of bone at an appropriate depth that would be particularly useful for distinguishing normal bone marrow from bone marrow that exhibits pre-clinical changes associated with incipient osteoporosis or osteopenia. For example, FIG. 5 shows a bone depth profile 500, measuring NMR signal strength, approximately proportional to the density of hydrogen atoms, on vertical axis 502, as a function of depth into the bone in millimeters, shown on horizontal axis 504. Curve 506 in plot 500 shows a peak at a depth of about 1.75 to 2.5 mm, in the center of the bone marrow, and a region 508, extending from 2.0 to 2.2 mm, was chosen for making comparisons of NMR parameters for the bones of the OVX and sham operated rats. These NMR parameters, listed at 410 of FIG. 4, include T1 measurements using a saturation recovery pulse sequence; T2 measurements using a CPMG-like sequence, optionally using the estimation method of signal processing described in Bergman et al to reduce the effects of noise; and ADC measurement, using a Stray Field Gradient Stimulated Echo pulse sequence.

Figure 6:
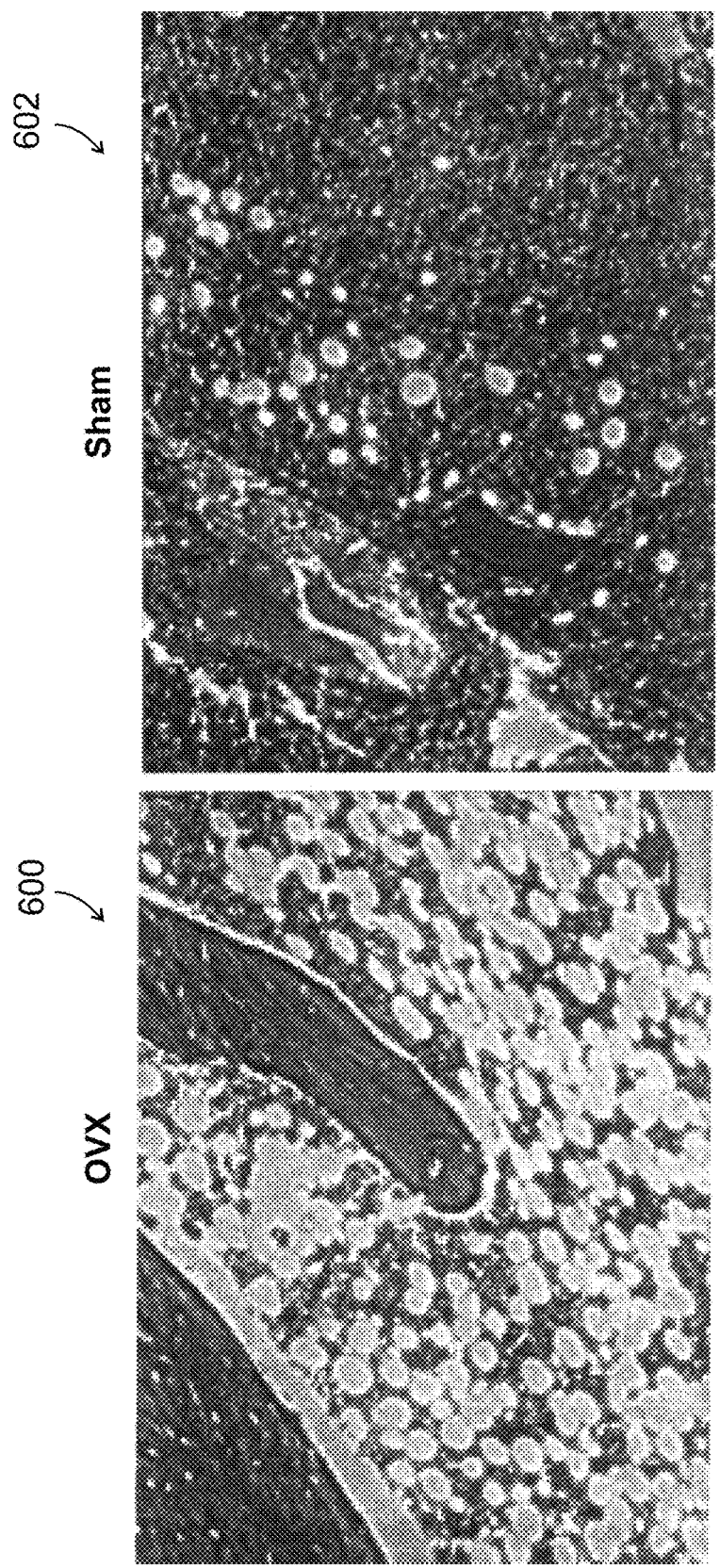
FIG. 6 shows histology images showing difference in appearance of bone marrow in rats which have and have not had ovariectomies, in the experiments outlined in FIG. 4.

Micro-radiography measurements listed at 412 include bone mass density measurements, and comparison of the microradiography images with the histology measurements listed at 414. The histology measurements comprised qualitative indications of different cell types, such as adipocytes and blood cells. FIG. 6 shows histology image 600, made from the medullary cavity of an OVX rat, and histology image 602, made from the medullary cavity of a sham operated rat, in both cases 3.5 months after the operation. Image 600 shows a much greater concentration of adipocytes, the light-colored cells visible in the two images, than image 602.

Figure 7:
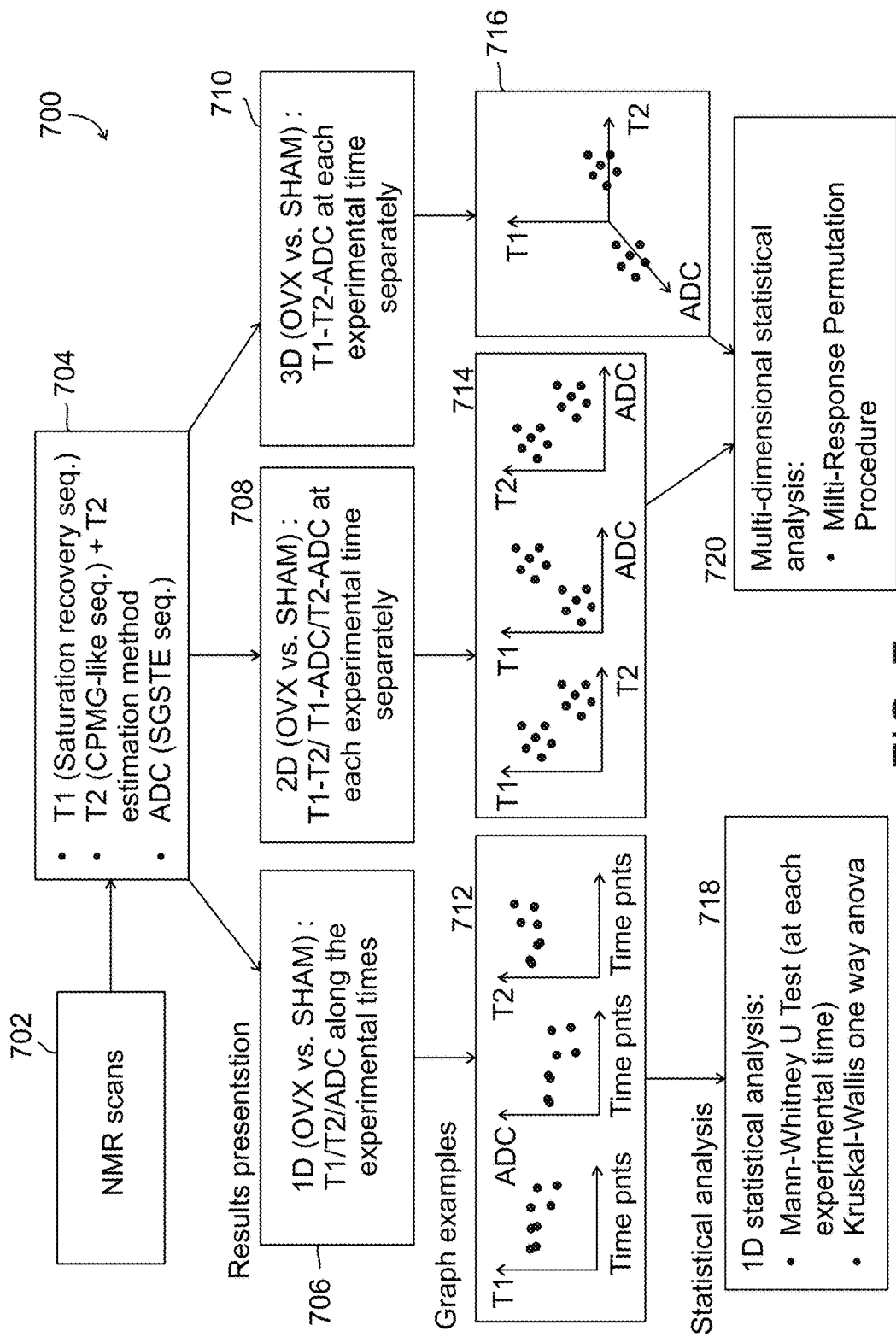
FIG. 7 is a chart illustrating methods used to analyze data on NMR parameters, in the experiments outlined in FIG. 4.

FIG. 7 shows a chart 700 outlining how the results are presented, and how the data was analyzed, for the NMR scans performed, as stated in box 702. Box 704 lists the different NMR parameters measured, and the NMR pulse sequences used to measure them, as described above in box 410 of FIG. 4. Different ways of presenting the results are listed in boxes 706, 708, and 710. Box 706 describes one-dimensional ways of plotting the results, comparing one of the NMR parameters, T1, T2, or ADC, for the OVX bones and the sham operated bones. Examples of such graphs are schematically shown in box 712. Box 708 lists two-dimensional ways of plotting the results, plotting one of the three NMR parameters against another one, for example T1 vs. T2, or T1 vs. ADC, or T2 vs. ADC. Box 714 schematically shows such scatter plots. For these plots, data from different sets of bones (OVX or sham operated), and data from different times after the operation, for example 3.5 months or 4.5 months, are optionally distinguished by using different symbols for the points plotted. Box 710 describes a three-dimensional way of plotting the results, plotting all three NMR parameters, T1, T2, and ADC in a single three-dimensional perspective plot, as shown schematically in box 716. Although such a three-dimensional perspective plot may not unambiguously show the three coordinate values for each point, if the perspective plot is made from a suitably chosen point of view, then the points for the OVX bones may be seen to be clustered separately from the points for the sham operated bones, possibly with a clearer separation than in the two-dimensional scatter plots as may be seen in the three-dimensional scatter plot shown schematically in box 716. Such plots optionally show only points for measurements made at a given time after the operation, e.g. only for 3.5 months, or only for 4.5 months.

Box 718 lists statistical tests that were used to determine the statistical significance of the differences in values, for OVX bones and sham operated bones, for a given NMR parameter at a time, T1, T2, or ADC. These tests include the Mann-Whitney U Test, applied at for measurements made at a given time after the operation, and the Kruskal-Wallis one way anova test. Statistically significant differences were found, for each NMR parameter, for measurements made at 3.5 months and at 4.5 months after the operation, using 16 OVX bones and 16 sham operated bones in each case. Box 720 lists a multi-dimensional statistical analysis test that was performed for the two-dimensional and three-dimensional scatter plots, the Multi-Response Permutation Procedure. Again, statistically significant differences were found between the OVX bones and the sham operated bones, for measurements made at 3.5 months and at 4.5 months after the operation.

Figure 8:
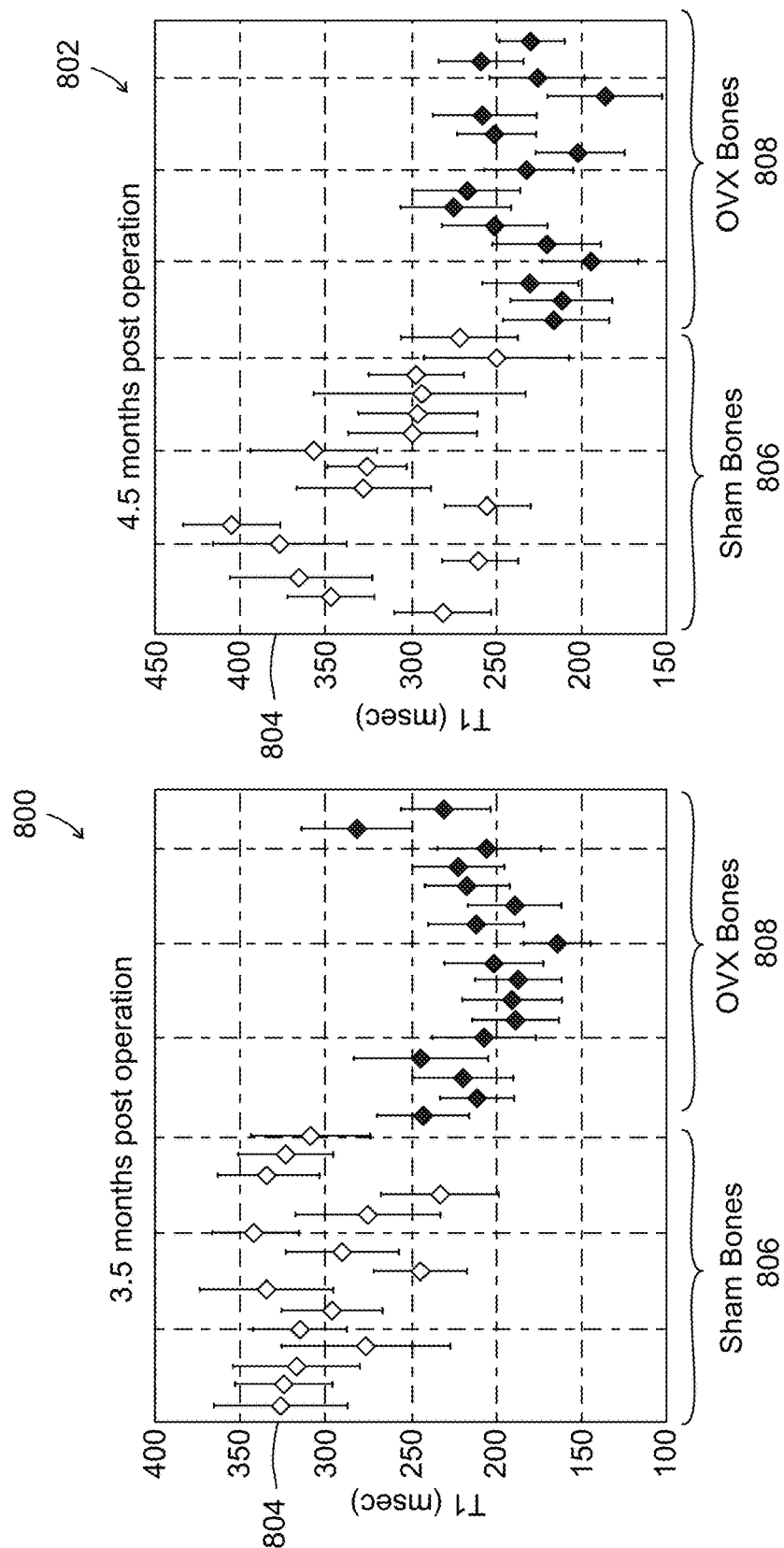
FIG. 8 shows plots of T1 measurements in the bone marrow of rats, showing differences between rats that have had and have not had ovariectomies, in the experiments outlined in FIG. 4.

FIG. 8 shows a plot 800 of T1 for OVX bones and sham operated bones, 3.5 months after the operation, and a similar plot 802 for OVX bones and sham operated bones, 4.5 months after the operation. In each plot, vertical axis 804 shows T1 in milliseconds. The data for the sham operated bones 806 is grouped together on the left side of each plot, and the data for the OVX bones 808 is grouped together on the right side of each plot. It is apparent, from looking at the these plots, that there is a considerable difference between the T1 values for the OVX bones and the sham operated bones, with lower values for the OVX bones, as might be expected for bone marrow with a higher fat content.

Figure 9A:
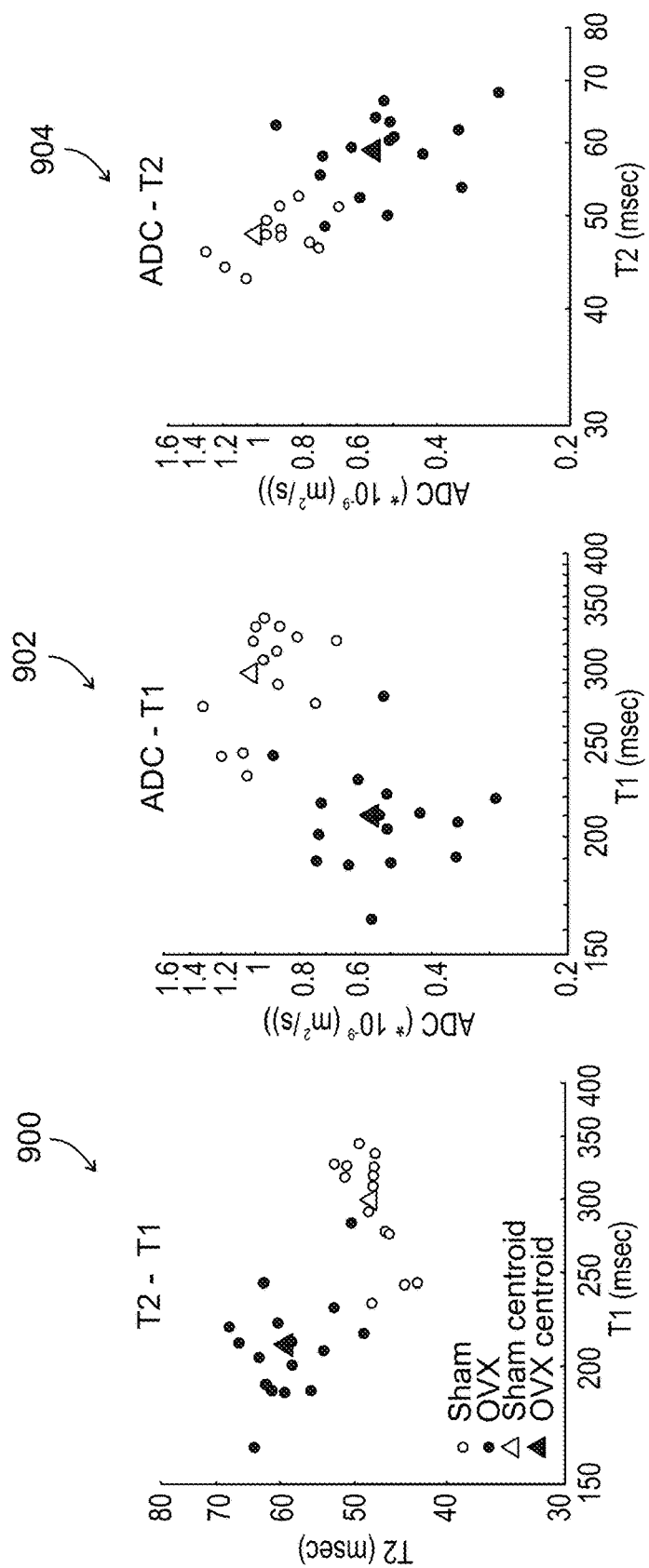
FIGS. 9A and 9B show two-dimensional scatter plots of NMR parameters in the bone marrow of rats that have had and have not had ovariectomies, in the experiments outlined in FIG. 4.
Figure 9B:
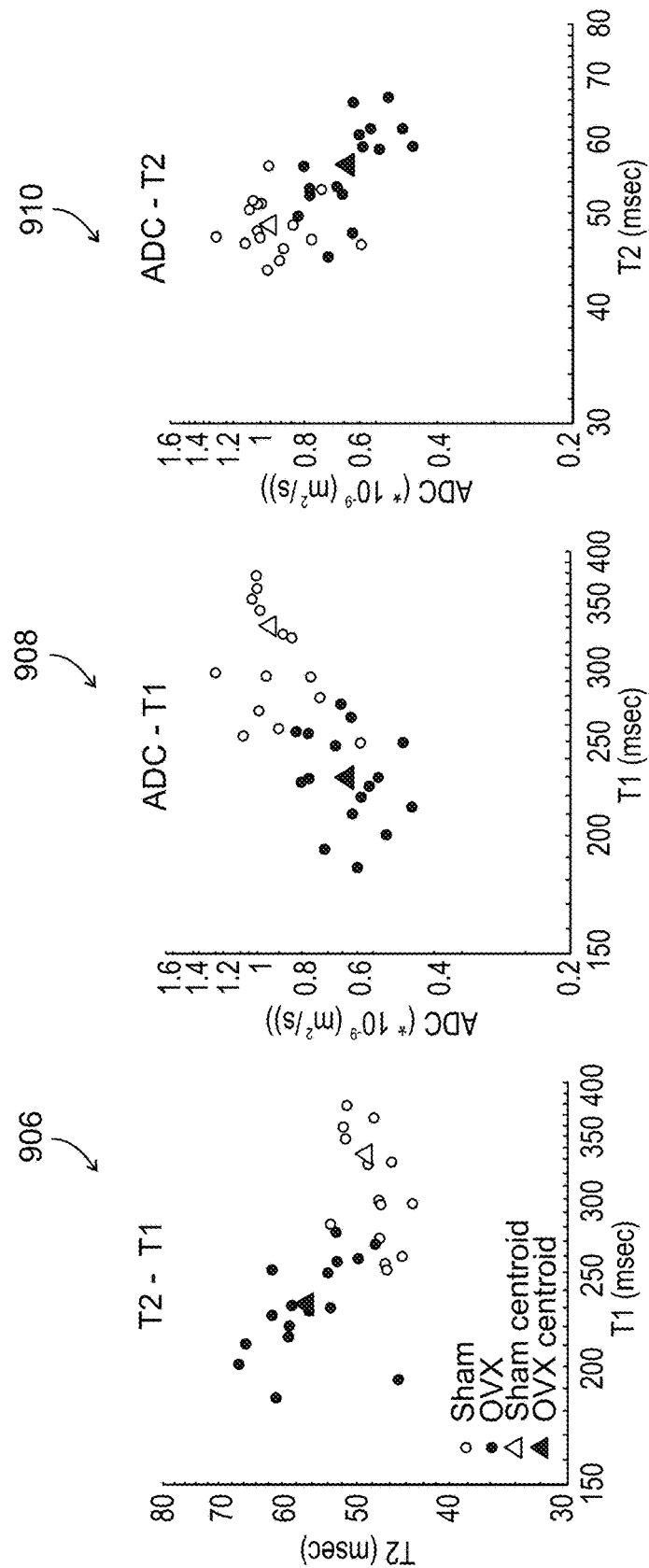

FIGS. 9A and 9B show two-dimensional scatter plots for measurements of T1, T2, and ADC, measured in 16 bones each for the sham operated rats and for the OVX rats. In FIG. 9A, plots 900, 902, and 904 respectively show T2 vs. T1, ADC vs. T1, and ADC vs. T2, for measurements made 3.5 months after the operation. The two clusters, for sham operated and OVX rats, are well separated in each of the plots. The centroid of each cluster is indicated by a triangle, in each plot. In FIG. 9B, plots 906, 908, and 910 respectively show T2 vs. T1, ADC vs. T1, and ADC vs. T2, for measurements made 4.5 months after the operation. Again the two clusters are well separated in each plot.

Table 1 shows the mean and standard deviation values for T1, T2, and ADC measurements, for each set of bones (OVX bones and sham operated bones), at each of two times after the operation, 3.5 months and 4.5 months.

TABLE 1

Comparison of T1, T2, and ADC values for OVX and sham operated bones

| | 3.5 months Sham | 3.5 months OVX | 4.5 months Sham | 4.5 months OVX |
| --- | --- | --- | --- | --- |
| T1 (msec) | 313 ± 35 | 232 ± 30 | 299 ± 35 | 208 ± 30 |
| ADC ($10^{-9}$ m$^2$/s) | 1.03 ± 0.2 | 0.55 ± 0.15 | 0.95 ± 0.17 | 0.63 ± 0.14 |
| T2 (msec) | 48 ± 1.7 | 58.5 ± 1.5 | 48.5 ± 1.7 | 56 ± 1.2 |

It is apparent from Table 1 that, for both the 3.5 month and 4.5 month cases, T1 and ADC are significantly lower for OVX bones than for sham operated bones, and T2 is significantly higher for OVX bones than for sham operated bones. That is the result that might be expected if OVX bones have higher fat content in the marrow than sham operated bones, since fat generally has lower T1 and ADC, and higher T2, than mesenchymal stem cell tissue, the other major constituent of bone marrow.

Table 2 shows the mean and standard deviation values, in milliseconds, for measurements of T2, for three groups of bones: sham operated bones, OVX bones from rats that were not given parathyroid hormone therapy (PTH), and OVX bones from rats that were given parathyroid hormone therapy after the ovariectomy (labeled "OVX+PTH" in Table 2). The comparison is made for both the central zone and the peripheral zone of the bone marrow.

TABLE 2

Comparison of T2 (in msec) for sham operated bones, and for OVX bones with and without parathyroid hormone therapy (PTH)

| | Sham | OVX | OVX + PTH |
|---|---|---|---|
| Peripheral zone | 34 ± 2 | 41 ± 1.5 | 31.5 ± 1.5 |
| Central zone | 47 ± 1.5 | 48.5 ± 1.5 | 46 ± 1.5 |

Although the differences between the sham operated and OVX bones, with and without PTH, are only marginally significant for the central zone of the bone marrow, the differences are significant for the peripheral zone. In the peripheral zone, the OVX bones without PTH have significantly higher T2 than the sham operated bones, as expected if the marrow has a higher number fat content. But for the OVX rats that received PTH, the T2 value is significant lower than for the OVX rats without PTH, and even somewhat lower than for the sham operated rats. It seems that PTH can reverse the effects of ovariectomy on bone marrow, and that this reversal is detectable in NMR measurements, at least in the peripheral zone of the bone marrow. This result supports the idea that NMR measurements in bone marrow can be used to monitor the efficacy of drug therapy designed to prevent osteoporosis and osteopenia even in subjects without clinical symptoms of those conditions, as described for example in FIG. 3.

Possible Treatments for Pre-Clinical Bone Deficiency

The following list includes optional treatments that a patient diagnosed with bone inhibition at an early, preclinical stage, in accordance with some embodiments of the invention, may be prescribed with. (Bernabei R, Martone A M, Ortolani E, Landi F, Marzetti E. (2014). "Screening, diagnosis and treatment of osteoporosis: a brief review in Clinical Cases in Mineral and Bone Metabolism" 2014; 202 11(3): 201-207.)

Non-pharmacological treatments

Many strategies are available to prevent osteoporosis and its complications, such as supplementation with calcium (500-1,000 mg daily) and vitamin D, physical activity and multidisciplinary interventions to decrease the risk of falls (5). These premises also represent the basis for every specific pharmacological treatment, since calcium and vitamin D deficiency is the most common cause of non-responsiveness to anti-osteoporotic medications.

Vitamin D Supplementation

The major active metabolite of vitamin D, 1α,25-dihydroxy-colecalciferol [1,25 (OH)2D3] derives for 80% from the conversion of 7-dehydrocholesterol by UV light and 20% from the diet, in particular blue fish and dairy products. The vitamin D precursor is liposoluble and settles mostly in the adipose tissue. The free quota is converted in the liver into 25-hydroxycolecalciferol [25 (OH) D], the major circulating vitamin D metabolite, whose levels are the most reliable index of vitamin D status. 25 (OH) D is converted into the active metabolite in the kidney, through a complex homeostatic mechanism involving parathyroid hormone (PTH) and calcium and phosphorus serum levels (6).

Physical activity is highly effective in attenuating the age-related bone massloss (16, 17). It is therefore recommended to carry out a minimum of activity (for example, 30 minutes of walk daily) for its positive effects on bone mass and the risk of falling (18).

Drugs

Pharmacological agents against osteoporosis either decrease bone resorption to produce secondary gains in bone mass or directly stimulate increases in bone mass (20). A brief overview of the main drugs currently available to treat osteoporosis is provided in the following subsections.

Bisphosphonates: Bisphosphonates are synthetic compounds with anti-resorptive activity (21). They act on bone through binding to hydroxyapatite and inhibiting osteoclast activation.

Denosumab: Denosumab is a human monoclonal antibody that blocks the interaction of receptor activator of nuclear factor kB ligand (RANKL) with receptor activator of nuclear factor kB (RANK), whereby inhibiting bone resorption strongly and rapidly (51).

Hormone replacement therapy (HRT): Treatment of osteoporotic women with HRT to prevent fractures has been a long-standing controversial issue. Estrogen replacement, alone or in combination with tibolone (a synthetic steroid with estrogenic and androgenic properties), increases bone mass (58).

Selective estrogen receptor modulators (SERMs): SERMs are synthetic molecules that bind to the estrogen receptor thereby acting as estrogen agonists on bone and liver and as antagonists on breast and genitor-urinary tract. Raloxifene at the dose of 60 to 120 mg daily increases BMD by 2 to 3% at the lumbar spine and femoral neck (59, 60). Based on data from the MORE study, raloxifene reduces the incidence of vertebral fractures by 40 to 50%, with no effect on non-vertebral fractures (61).

Recombinant human PTH: Recombinant 1-34 fragment of human PTH—rhPTH(1-34)teriparatide—and recombinant human intact PTH—rh-PTH(1-84)-stimulate bone remodeling by inducing an increase in bone formation followed by a slower increase in bone resorption (72). They strongly increase BMD in the trabecular compartment, whereas their effect appears lower than bisphosphonates in the cortical sites."

It is expected that during the life of a patent maturing from this application relevant new NMR parameters may be developed and the scope of the term "NMR parameters" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for monitoring treatment of bone deficiency in a patient, comprising:
   collecting NMR signals of a bone marrow volume in a bone of the patient, at a first time point, using a stray field non-homogeneous NMR scanner;
   repeating the collecting of NMR signals at least at a second time point, at least six weeks after the first time point;
   the patient receiving a treatment for bone deficiency, between the first time point and the second time point;
   analyzing the NMR signals collected at the first time point and the second time point, comprising estimating one or both of adipose tissue content and changes in adipose tissue content of the bone marrow, providing feedback on the treatment.

2. The method according to claim 1, wherein the bone of the patient has normal bone density levels which are not indicative of bone deficiency as indicated by X-ray.

3. The method according to claim 1, wherein said analyzing comprises extracting, from said collected NMR signals, at least one parameter out of: T1 relaxation time, T2 relaxation time, T2* relaxation time, and apparent diffusion coefficient.

4. The method according to claim 1, wherein said adipose tissue content comprises at least one of a volume fraction of adipocytes and a population of adipocytes in said bone marrow volume.

5. The method according to claim 1, wherein estimating comprises using one or both of a ratio between T1 and T2 and a ratio between T1 and T2* to indicate changes in adipose tissue content.

6. The method according to claim 1, wherein repeating the collecting of NMR signals is done also at one or more additional time points, and the method also comprises analyzing the NMR signals collected at the additional time points, providing additional feedback on the treatment.

7. The method according to claim 1, wherein said method is performed without applying imaging pulses to said bone marrow volume.

8. The method according to claim 1, wherein collecting the NMR signals the second time is done before changes in bone density in response to said treatment can be detected using X-ray.

9. The method according to claim 1, wherein said treatment is in the form of one or more of use of pharmaceutical agents, a dietary change, and a change in physical activity.

10. The method according to claim 1, further comprising performing a scout scan of said bone to locate said bone marrow volume.

11. The method according to claim 1, wherein said analyzing comprises performing at least one of a one dimensional and multi-dimensional analysis of one or more of T1 relaxation time, T2 relaxation time, T2* relaxation time, and ADC, extracted from said collected NMR signals.

12. A method for monitoring treatment of bone deficiency in a patient, comprising:
   collecting NMR signals of a bone marrow volume in a bone of the patient, at a first time point, without applying imaging pulses to the bone marrow volume;
   repeating the collecting of NMR signals at least at a second time point, at least six weeks after the first time point;
   the patient receiving a treatment for bone deficiency, between the first time point and the second time point;
   analyzing the NMR signals collected at the first time point and the second time point, comprising estimating one or both of adipose tissue content and changes in adipose tissue content of the bone marrow, providing feedback on the treatment.

13. A method for monitoring treatment of bone deficiency in a patient, comprising:
   collecting NMR signals of a bone marrow volume in a bone of the patient, at a first time point;
   repeating the collecting of NMR signals at least at a second time point, at least six weeks after the first time point;

the patient receiving a treatment for bone deficiency, between the first time point and the second time point;

analyzing the NMR signals collected at the first time point and the second time point, comprising using one or both of a ratio between T1 and T2 and a ratio between T1 and T2* to indicate changes in adipose tissue content of the bone marrow, providing feedback on the treatment.

* * * * *